US007635385B2

(12) United States Patent
Milliman et al.

(10) Patent No.: US 7,635,385 B2
(45) Date of Patent: Dec. 22, 2009

(54) ANASTOMOSIS INSTRUMENT AND METHOD FOR PERFORMING SAME

(76) Inventors: Keith Milliman, 5 Marywood Rd., Bethel, CT (US) 06801; Kevin Sniffen, 38 Grand St., Danbury, CT (US) 06810; David A. Nicholas, 148 Cottage St., Trumbull, CT (US) 06611; Scott E. Manzo, 272 E. Village Rd., Shelton, CT (US) 06484; Peter Hinchliffe, 285 Central Ave., New Haven, CT (US) 06515

( * ) Notice: Subject to any disclaimer, the term of this patent is extended or adjusted under 35 U.S.C. 154(b) by 494 days.

(21) Appl. No.: 11/429,583

(22) Filed: May 5, 2006

(65) Prior Publication Data

US 2006/0206124 A1 Sep. 14, 2006

Related U.S. Application Data

(63) Continuation of application No. 10/388,969, filed on Mar. 13, 2003, now Pat. No. 7,204,843, which is a continuation of application No. 09/882,245, filed on Jun. 14, 2001, now abandoned, which is a continuation of application No. 09/410,817, filed on Oct. 1, 1999, now abandoned, which is a continuation-in-part of application No. 09/256,260, filed on Feb. 23, 1999, now Pat. No. 6,083,234, which is a continuation-in-part of application No. 08/877,701, filed on Jun. 17, 1997, now Pat. No. 6,024,748, which is a continuation-in-part of application No. 08/685,385, filed on Jul. 23, 1996, now Pat. No. 5,707,380.

(51) Int. Cl.
 *A61F 2/06* (2006.01)

(52) U.S. Cl. ............... 623/1.23; 606/153; 606/213; 227/180.1
(58) Field of Classification Search ............... 606/153, 606/213, 219, 139, 253, 149; 227/180.1, 227/176.1, 19, 179.1
See application file for complete search history.

(56) References Cited

U.S. PATENT DOCUMENTS 2,705,323 A * 4/1955 Bossong ............... 227/11

(Continued)

FOREIGN PATENT DOCUMENTS

EP 384647 A1 2/1990

(Continued)

OTHER PUBLICATIONS

International Search Report—EPO 97112634—Dec. 18, 1997.
International Search Report—EPO 98110977—Sep. 25, 1998.
International Search Report—EPO 99118064—Nov. 1, 2000.

(Continued)

*Primary Examiner*—(Jackie) Tan-Uyen T. Ho
*Assistant Examiner*—Christina Lauer

(57) ABSTRACT

A surgical instrument for anastomosis of first and second blood vessels includes a housing having distal and proximal ends, a handle and a disposable loading unit removably mounted to the distal end of the housing. The loading unit includes upper and lower fastener support members having a passage defined therethrough for receiving an end of the second blood vessel and configured to releasably support a plurality of surgical fasteners. The loading unit also includes a retractable anvil located at a distal end of the loading unit, the anvil being movable relative to the fastener support member in response to actuation of the handle to simultaneously deform the of surgical fasteners.

36 Claims, 24 Drawing Sheets

U.S. PATENT DOCUMENTS

| | | |
|---|---|---|
| 2,968,041 A | 1/1961 | Skold |
| 3,041,616 A * | 7/1962 | Henning et al. ............... 227/11 |
| 3,152,336 A | 10/1964 | Brady |
| 3,232,089 A | 2/1966 | Samuels et al. |
| 3,254,650 A | 6/1966 | Collito |
| 3,297,033 A | 1/1967 | Schmitt et al. |
| 3,366,301 A | 1/1968 | Mallina |
| 3,477,423 A | 11/1969 | Griffith |
| 3,496,939 A | 2/1970 | Odiaga et al. |
| 3,519,187 A | 7/1970 | Kapitanov et al. |
| 3,575,038 A | 4/1971 | Mallett |
| 3,741,025 A | 6/1973 | Russell |
| 3,771,526 A | 11/1973 | Rudie |
| 3,776,237 A | 12/1973 | Hill et al. |
| 3,856,016 A | 12/1974 | Davis |
| 3,908,662 A | 9/1975 | Razlov et al. |
| 3,954,108 A | 5/1976 | Davis |
| 3,974,835 A | 8/1976 | Hardy, Jr. |
| 4,018,228 A | 4/1977 | Goosen |
| 4,152,920 A | 5/1979 | Green |
| 4,166,466 A | 9/1979 | Jarvik |
| 4,182,339 A | 1/1980 | Hardy, Jr. |
| 4,201,314 A | 5/1980 | Samuels et al. |
| 4,216,776 A | 8/1980 | Downie et al. |
| 4,242,902 A | 1/1981 | Green |
| 4,299,224 A | 11/1981 | Noiles |
| 4,304,236 A * | 12/1981 | Conta et al. ............... 227/179.1 |
| 4,316,468 A | 2/1982 | Klieman et al. |
| 4,321,002 A | 3/1982 | Froehlich |
| 4,325,376 A | 4/1982 | Klieman et al. |
| 4,350,160 A | 9/1982 | Kolesov et al. |
| 4,368,736 A | 1/1983 | Kaster |
| 4,372,316 A | 2/1983 | Blake, III et al. |
| 4,408,603 A | 10/1983 | Blake, III et al. |
| 4,412,539 A | 11/1983 | Jarvik |
| 4,425,915 A | 1/1984 | Ivanov |
| 4,430,997 A | 2/1984 | DiGiovanni et al. |
| 4,452,376 A | 6/1984 | Klieman et al. |
| 4,466,436 A | 8/1984 | Lee |
| 4,467,804 A | 8/1984 | Hardy et al. |
| 4,476,863 A | 10/1984 | Kanshin et al. |
| 4,480,640 A | 11/1984 | Becht |
| D276,650 S | 12/1984 | Green et al. |
| 4,488,543 A | 12/1984 | Tornier |
| 4,493,317 A | 1/1985 | Klaue |
| 4,503,848 A | 3/1985 | Caspar et al. |
| 4,509,518 A | 4/1985 | McGarry et al. |
| 4,522,207 A | 6/1985 | Klieman et al. |
| 4,532,925 A | 8/1985 | Blake, III et al. |
| 4,534,351 A | 8/1985 | Rothfuss et al. |
| 4,552,148 A | 11/1985 | Hardy et al. |
| 4,586,503 A | 5/1986 | Kirsch et al. |
| 4,598,711 A | 7/1986 | Deniega |
| 4,611,595 A | 9/1986 | Klieman et al. |
| 4,616,650 A | 10/1986 | Green et al. |
| 4,671,445 A | 6/1987 | Barker et al. |
| 4,700,703 A | 10/1987 | Resnick et al. |
| 4,708,141 A | 11/1987 | Inoue et al. |
| 4,733,664 A | 3/1988 | Kirsch et al. |
| 4,752,024 A | 6/1988 | Green et al. |
| 4,759,364 A | 7/1988 | Boebel |
| 4,766,898 A | 8/1988 | Hardy et al. |
| 4,809,695 A | 3/1989 | Gwathmey et al. |
| 4,821,939 A | 4/1989 | Green |
| 4,872,874 A | 10/1989 | Taheri |
| 4,874,122 A | 10/1989 | Froelich et al. |
| 4,893,622 A | 1/1990 | Green et al. |
| 4,899,744 A | 2/1990 | Fujitsuka et al. |
| 4,907,591 A | 3/1990 | Vasconcellos et al. |
| 4,917,114 A | 4/1990 | Green et al. |
| 4,929,240 A | 5/1990 | Kirsch et al. |
| 4,930,674 A | 6/1990 | Barak |
| 4,931,057 A | 6/1990 | Cummings et al. |
| 4,957,499 A | 9/1990 | Lipatov et al. |
| 4,979,954 A | 12/1990 | Gwathmey et al. |
| 4,983,176 A | 1/1991 | Cushman et al. |
| 5,025,779 A | 6/1991 | Bugge |
| 5,030,226 A | 7/1991 | Green et al. |
| 5,057,111 A | 10/1991 | Park |
| 5,104,395 A | 4/1992 | Thornton et al. |
| 5,108,395 A | 4/1992 | Laurain |
| 5,112,343 A | 5/1992 | Thornton |
| 5,122,150 A | 6/1992 | Puig |
| 5,127,912 A | 7/1992 | Ray et al. |
| 5,129,913 A | 7/1992 | Ruppert |
| 5,147,361 A | 9/1992 | Ojima et al. |
| 5,188,638 A | 2/1993 | Tzakis |
| 5,192,288 A | 3/1993 | Thompson et al. |
| 5,192,294 A | 3/1993 | Blake, III |
| 5,205,459 A * | 4/1993 | Brinkerhoff et al. ...... 227/179.1 |
| 5,211,649 A | 5/1993 | Kohler et al. |
| 5,222,963 A | 6/1993 | Brinkerhoff et al. |
| 5,224,951 A | 7/1993 | Freitas |
| 5,234,447 A | 8/1993 | Kaster et al. |
| 5,250,058 A | 10/1993 | Miller et al. |
| 5,282,810 A | 2/1994 | Allen et al. |
| 5,314,436 A | 5/1994 | Wilk |
| 5,324,290 A | 6/1994 | Zdeblick et al. |
| 5,340,360 A | 8/1994 | Stefanchik |
| 5,346,115 A | 9/1994 | Perouse et al. |
| 5,346,501 A | 9/1994 | Regula et al. |
| 5,354,304 A | 10/1994 | Allen et al. |
| 5,364,399 A | 11/1994 | Lowery et al. |
| 5,366,458 A | 11/1994 | Korthoff et al. |
| 5,366,462 A | 11/1994 | Kaster et al. |
| 5,366,479 A * | 11/1994 | McGarry et al. ............. 606/219 |
| 5,403,333 A | 4/1995 | Kaster et al. |
| 5,403,338 A | 4/1995 | Milo |
| 5,423,826 A | 6/1995 | Coates et al. |
| 5,425,738 A | 6/1995 | Gustafson et al. |
| 5,431,668 A | 7/1995 | Burbank, III et al. |
| 5,437,684 A | 8/1995 | Calabrese et al. |
| 5,439,156 A * | 8/1995 | Grant et al. ............... 227/179.1 |
| 5,443,198 A | 8/1995 | Viola et al. |
| 5,452,733 A | 9/1995 | Sterman et al. |
| 5,454,824 A | 10/1995 | Fontayne et al. |
| 5,474,732 A | 12/1995 | Korthoff et al. |
| 5,485,947 A | 1/1996 | Olson et al. |
| 5,486,187 A | 1/1996 | Schenck |
| 5,488,958 A | 2/1996 | Topel et al. |
| 5,501,698 A | 3/1996 | Roth et al. |
| 5,503,617 A | 4/1996 | Jako |
| 5,503,635 A | 4/1996 | Sauer et al. |
| D372,310 S | 7/1996 | Hartnett |
| 5,533,661 A * | 7/1996 | Main et al. ............... 227/176.1 |
| 5,549,612 A | 8/1996 | Yapp et al. |
| 5,643,305 A | 7/1997 | Al-Tameem |
| 5,649,937 A | 7/1997 | Bito et al. |
| 5,658,300 A | 8/1997 | Bito et al. |
| 5,669,918 A | 9/1997 | Balazs et al. |
| 5,693,064 A | 12/1997 | Arnold |
| 5,695,504 A | 12/1997 | Gifford, III et al. |
| 5,697,943 A | 12/1997 | Sauer et al. |
| 5,702,412 A | 12/1997 | Popov et al. |
| 5,707,380 A | 1/1998 | Hinchliffe et al. |
| 5,709,335 A * | 1/1998 | Heck ....................... 227/176.1 |
| 5,725,537 A | 3/1998 | Green et al. |
| 5,732,872 A | 3/1998 | Bolduc et al. |
| 5,762,256 A | 6/1998 | Mastri et al. |
| 5,779,718 A | 7/1998 | Green et al. |
| 5,797,931 A | 8/1998 | Bito et al. |
| 5,797,934 A | 8/1998 | Rygaard |
| 5,807,277 A | 9/1998 | Swaim |
| 5,817,113 A | 10/1998 | Gifford, III et al. |

| Patent/Pub. No. | Date | Name |
|---|---|---|
| 5,823,956 A | 10/1998 | Roth et al. |
| 5,827,316 A | 10/1998 | Young et al. |
| 5,829,447 A | 11/1998 | Stevens et al. |
| 5,833,698 A | 11/1998 | Hinchliffe et al. |
| 5,839,639 A | 11/1998 | Sauer et al. |
| 5,855,614 A | 1/1999 | Stevens et al. |
| 5,860,581 A | 1/1999 | Robertson et al. |
| 5,881,943 A | 3/1999 | Heck et al. |
| 5,891,160 A | 4/1999 | Williamson, IV et al. |
| 5,893,369 A | 4/1999 | Lemole |
| 5,904,697 A | 5/1999 | Gifford, III et al. |
| 5,906,625 A | 5/1999 | Bito et al. |
| 5,910,153 A | 6/1999 | Mayenberger |
| 5,916,226 A | 6/1999 | Tozzi |
| 5,944,730 A | 8/1999 | Nobles et al. |
| 5,944,736 A | 8/1999 | Taylor et al. |
| 5,947,363 A | 9/1999 | Bolduc et al. |
| 5,951,576 A | 9/1999 | Wakabayashi |
| 5,954,735 A | 9/1999 | Rygaard |
| 5,957,363 A | 9/1999 | Heck |
| 5,957,879 A | 9/1999 | Roberts et al. |
| 5,961,481 A | 10/1999 | Sterman et al. |
| 5,964,782 A | 10/1999 | Lafontaine et al. |
| 5,971,973 A | 10/1999 | Peters |
| 5,972,030 A | 10/1999 | Garrison et al. |
| 5,976,159 A | 11/1999 | Bolduc et al. |
| 5,976,164 A | 11/1999 | Bencini et al. |
| 5,989,277 A | 11/1999 | LeMaire, III et al. |
| 5,989,278 A | 11/1999 | Mueller |
| 5,993,464 A | 11/1999 | Knodel |
| 5,993,468 A | 11/1999 | Rygaard |
| 6,015,416 A | 1/2000 | Stefanchik et al. |
| 6,024,748 A | 2/2000 | Manzo et al. |
| 6,030,395 A | 2/2000 | Nash et al. |
| 6,036,705 A | 3/2000 | Nash et al. |
| 6,056,762 A | 5/2000 | Nash et al. |
| 6,066,144 A | 5/2000 | Wolf et al. |
| 6,080,173 A | 6/2000 | Williamson, IV et al. |
| 6,083,234 A | 7/2000 | Nicholas et al. |
| 6,110,187 A | 8/2000 | Donlon |
| 6,131,789 A | 10/2000 | Schulze et al. |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,176,867 B1 | 1/2001 | Wright |
| 6,179,849 B1 | 1/2001 | Yencho et al. |
| 6,183,486 B1 | 2/2001 | Snow et al. |
| 6,187,019 B1 | 2/2001 | Stefanchik et al. |
| 6,187,020 B1 | 2/2001 | Zegdi et al. |
| 6,187,022 B1 | 2/2001 | Alexander, Jr. et al. |
| 6,190,397 B1 | 2/2001 | Spence et al. |
| 6,190,590 B1 | 2/2001 | Randall et al. |
| 6,193,734 B1 | 2/2001 | Bolduc et al. |
| 6,197,042 B1 | 3/2001 | Ginn et al. |
| 6,206,913 B1 | 3/2001 | Yencho et al. |
| 6,224,603 B1 | 5/2001 | Marino |
| 6,231,506 B1 | 5/2001 | Hu et al. |
| 6,234,995 B1 | 5/2001 | Peacock, III |
| 6,241,741 B1 | 6/2001 | Duhaylongsod et al. |
| 6,241,742 B1 | 6/2001 | Spence et al. |
| 6,241,743 B1 | 6/2001 | Levin et al. |
| 6,248,117 B1 | 6/2001 | Blatter |
| 6,253,984 B1 | 7/2001 | Heck et al. |
| 6,254,615 B1 | 7/2001 | Bolduc et al. |
| 6,254,617 B1 | 7/2001 | Spence et al. |
| 6,280,460 B1 | 8/2001 | Bolduc et al. |
| 6,332,468 B1 | 12/2001 | Benetti |
| 6,338,712 B2 | 1/2002 | Spence et al. |
| 6,346,074 B1 | 2/2002 | Roth |
| 6,350,252 B2 | 2/2002 | Ray et al. |
| 6,361,543 B1 | 3/2002 | Chin et al. |
| 6,371,965 B2 | 4/2002 | Gifford, III et al. |
| 6,387,105 B1 | 5/2002 | Gifford, III et al. |
| 6,391,039 B1 | 5/2002 | Nicholas et al. |
| 6,401,721 B1 | 6/2002 | Maginot |
| 6,440,146 B2 | 8/2002 | Nicholas et al. |
| 6,443,965 B1 | 9/2002 | Gifford, III et al. |
| 6,450,390 B2 | 9/2002 | Heck et al. |
| 6,451,034 B1 | 9/2002 | Gifford, III et al. |
| 6,461,365 B2 | 10/2002 | Bolduc et al. |
| 6,471,713 B1 | 10/2002 | Vargas et al. |
| 6,494,889 B1 | 12/2002 | Fleischman et al. |
| 6,503,259 B2 | 1/2003 | Huxel et al. |
| 6,562,037 B2 | 5/2003 | Paton et al. |
| 6,682,540 B1 | 1/2004 | Sancoff et al. |
| 6,726,697 B2 | 4/2004 | Nicholas et al. |
| 6,769,594 B2 | 8/2004 | Orban, III |
| 6,818,009 B2 | 11/2004 | Hart et al. |
| 7,059,510 B2 | 6/2006 | Orban, III |
| 2003/0171775 A1 | 9/2003 | Belson |
| 2003/0181930 A1 | 9/2003 | Milliman et al. |
| 2003/0208213 A1 | 11/2003 | Manzo |
| 2004/0078047 A1 | 4/2004 | Nicholas et al. |
| 2004/0082963 A1 | 4/2004 | Gannoe et al. |
| 2004/0092971 A1 | 5/2004 | Sniffin et al. |
| 2004/0092998 A1 | 5/2004 | Sniffin et al. |
| 2004/0199182 A1 | 10/2004 | Milliman et al. |
| 2005/0010241 A1 | 1/2005 | Milliman et al. |
| 2005/0033359 A1 | 2/2005 | Dycus |
| 2006/0111731 A1 | 5/2006 | Manzo |

FOREIGN PATENT DOCUMENTS

| | | |
|---|---|---|
| EP | 594004 A1 | 4/1994 |
| EP | 643946 A | 3/1995 |
| EP | 656191 A2 | 6/1995 |
| EP | 820725 B1 | 7/1997 |
| EP | 820724 A | 1/1998 |
| EP | 885595 A1 | 12/1998 |
| EP | 1088519 A | 4/2001 |
| FR | 1518083 | 2/1968 |
| FR | 2777446 | 10/1999 |
| GB | 935490 | 8/1963 |
| WO | WO88/01486 | 3/1988 |
| WO | WO95/15715 | 6/1995 |
| WO | WO95/17127 | 6/1995 |
| WO | WO95/35065 | 12/1995 |
| WO | WO97/40754 | 11/1997 |
| WO | WO99/11178 | 3/1999 |
| WO | WO 00/09040 | 2/2000 |
| WO | WO 00/09092 | 2/2000 |
| WO | WO 00/33745 | 6/2000 |
| WO | WO00/69343 | 11/2000 |
| WO | WO 00/069343 | 11/2000 |
| WO | WO01/52748 | 7/2001 |
| WO | WO02/32323 | 4/2002 |
| WO | WO02/032324 | 4/2002 |
| WO | WO02/058568 | 8/2002 |
| WO | WO03/101314 | 12/2003 |

OTHER PUBLICATIONS

International Search Report—EPO 00120262—Dec. 20, 2000.
International Search Report—PCT/US01/02043—Nov. 7, 2001.
International Search Report—PCT/US03/18295—Oct. 28, 2003.
Information Booklet for: Ligaclip, Ligating Clips, Appliers & Removers for Security in Ligation, Ethicon, Inc., 1982.
Information Booklet for: Deep Surgery Advantage-Dramatic New access Plus Automatic-Feed in Vessel Ligation, Hemoclip ® Automatic Ligating Clip System, Edward Weck & Company, Inc. Sep. 1996.
Information Booklet for: Auto Suture® Premium Sugliclip™ Titanium Disposable Automatic Clip Appliers, United States Surgical Corporation, 1981.

* cited by examiner

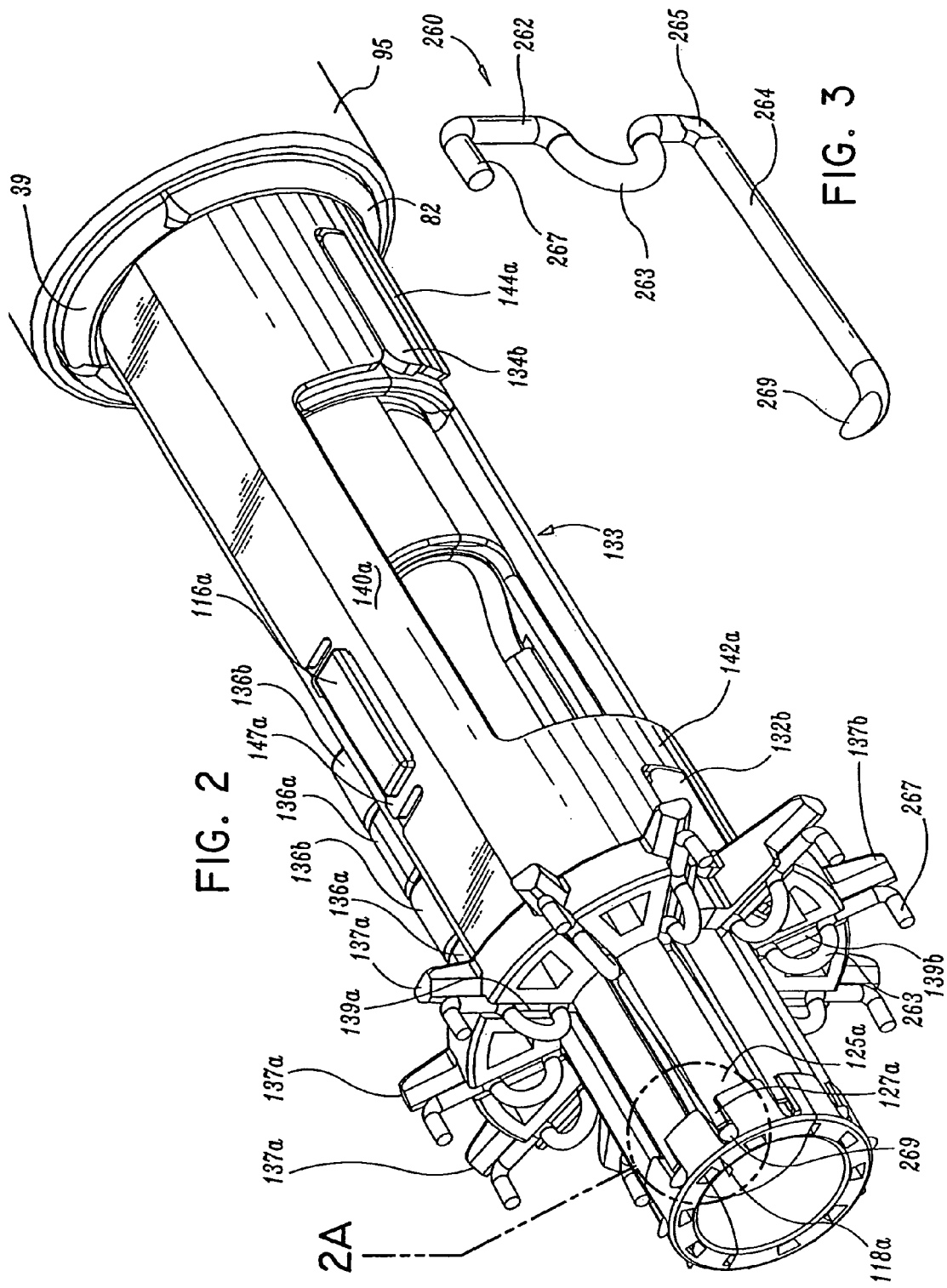

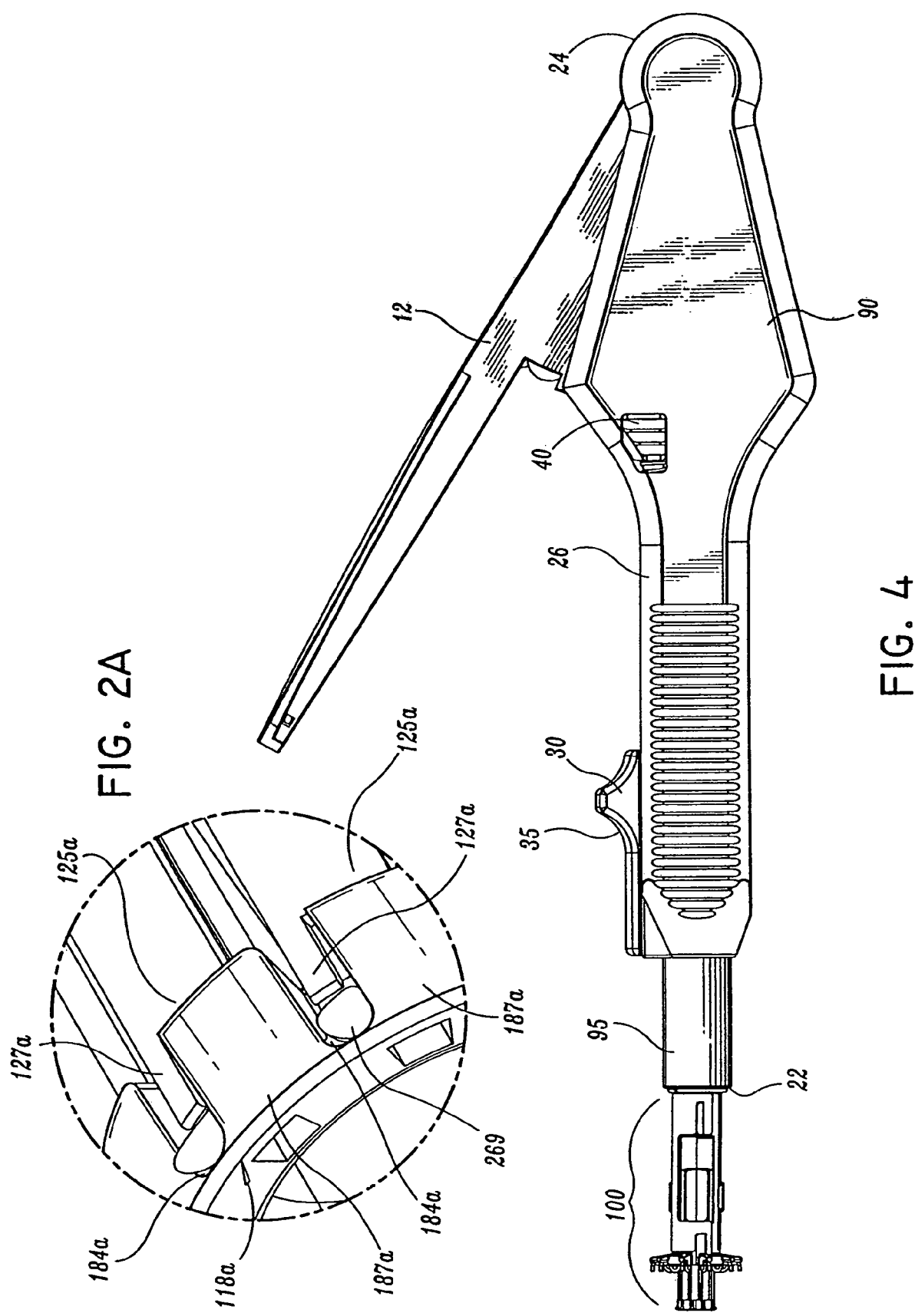

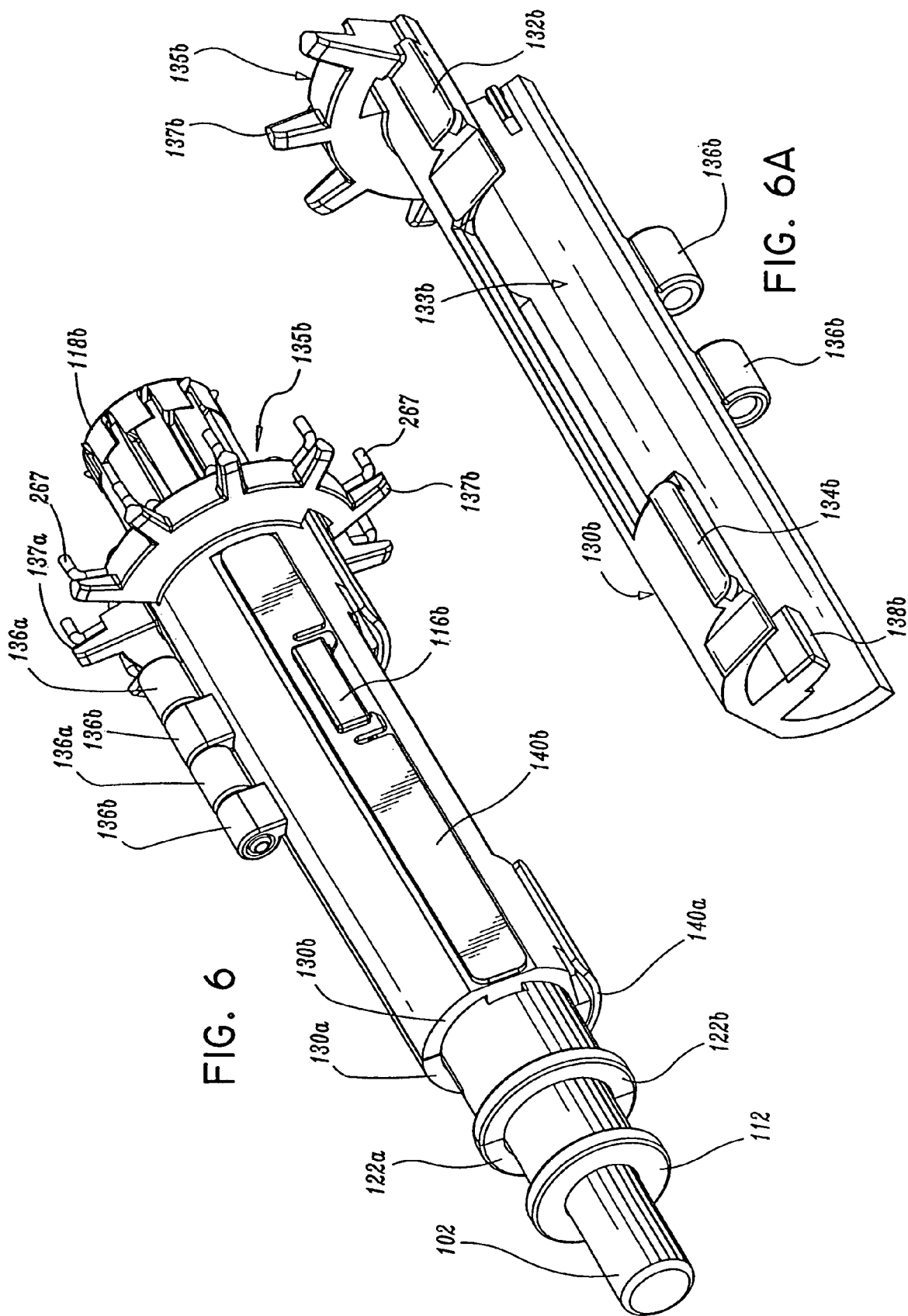

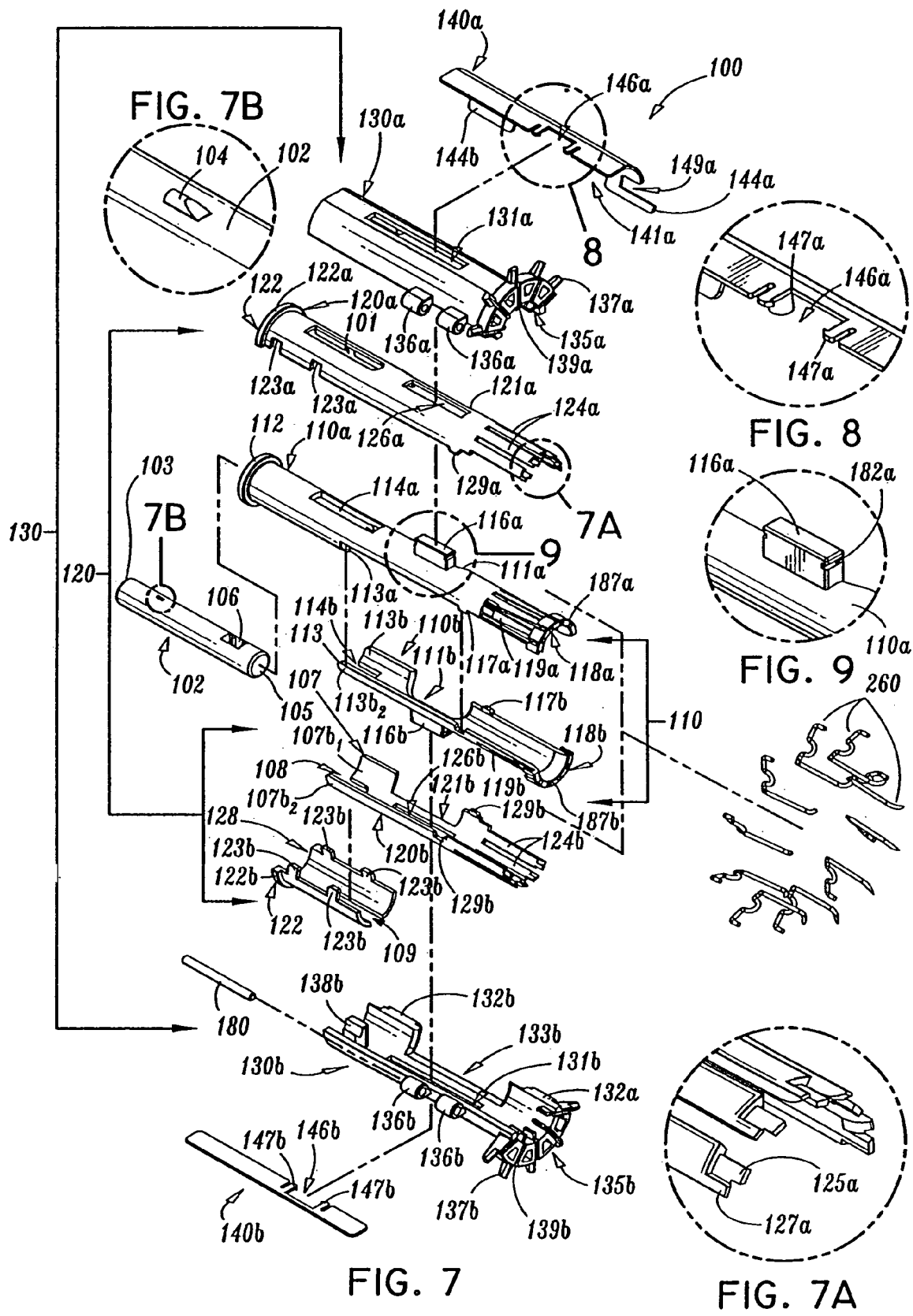

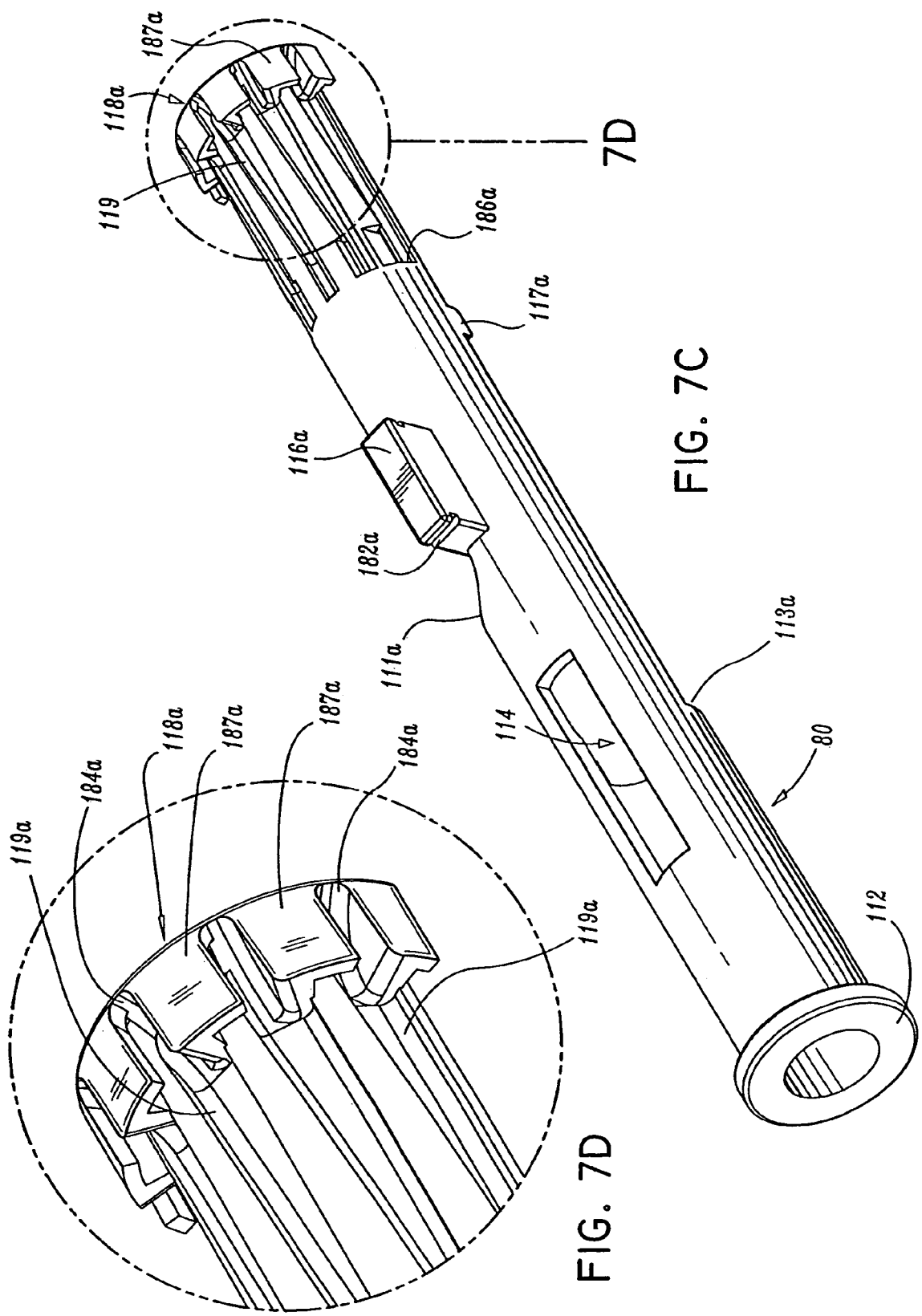

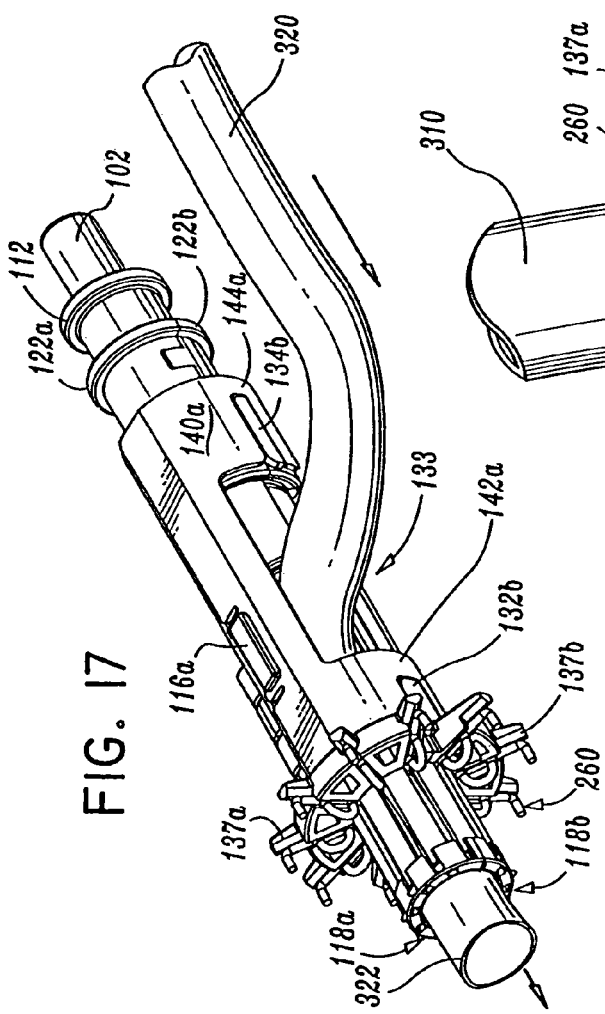
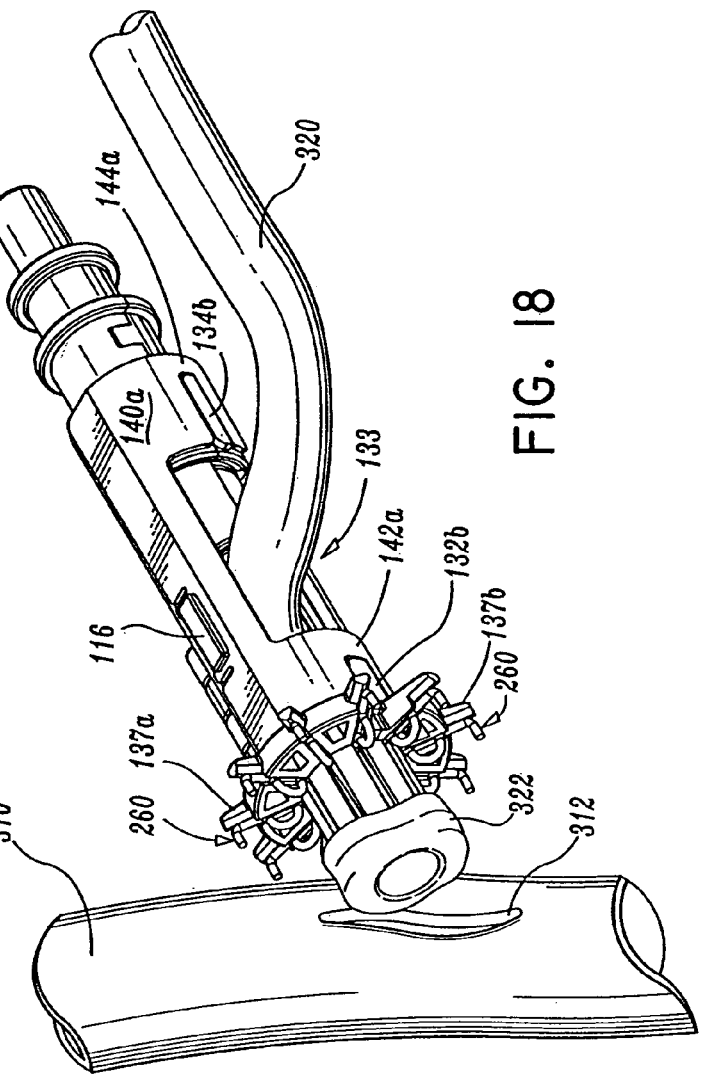
FIG. 17
FIG. 18

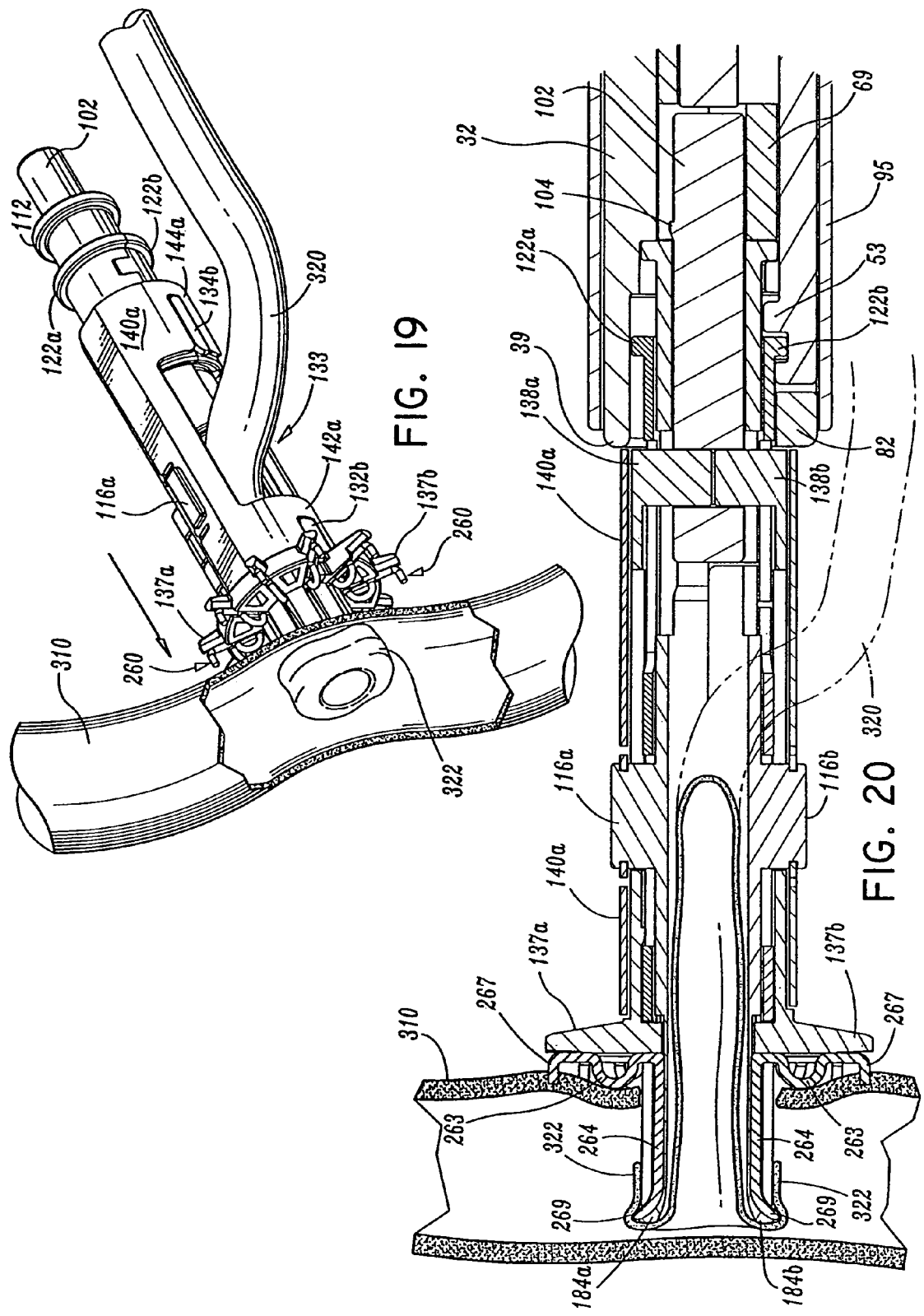

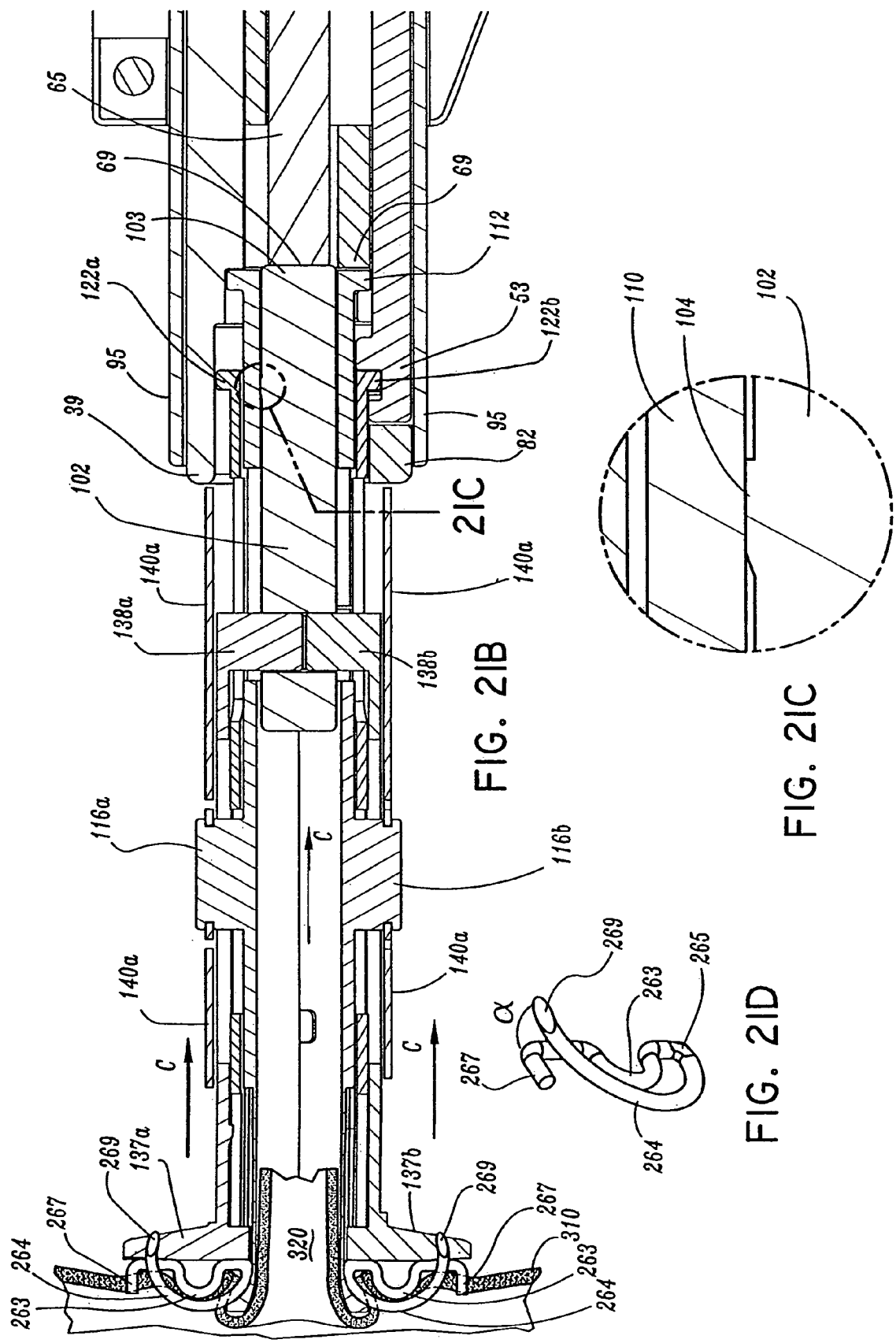

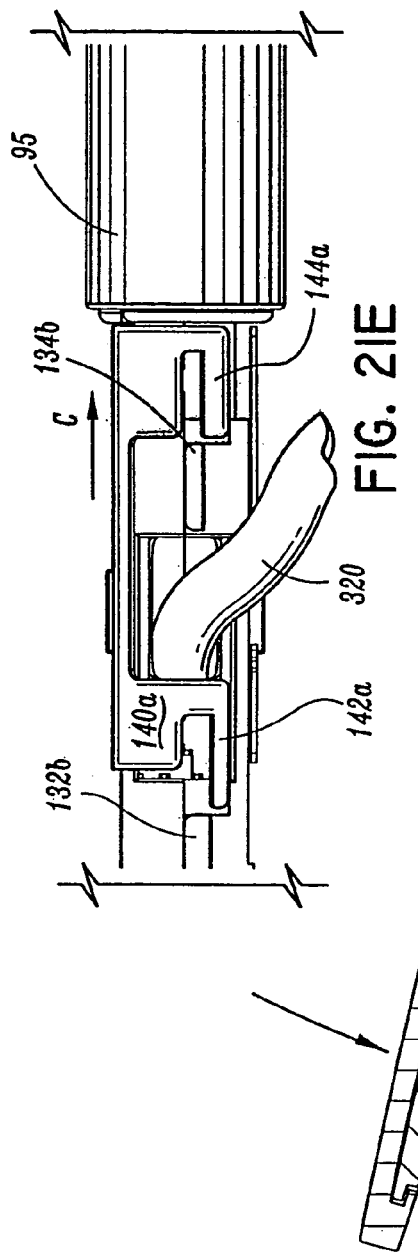
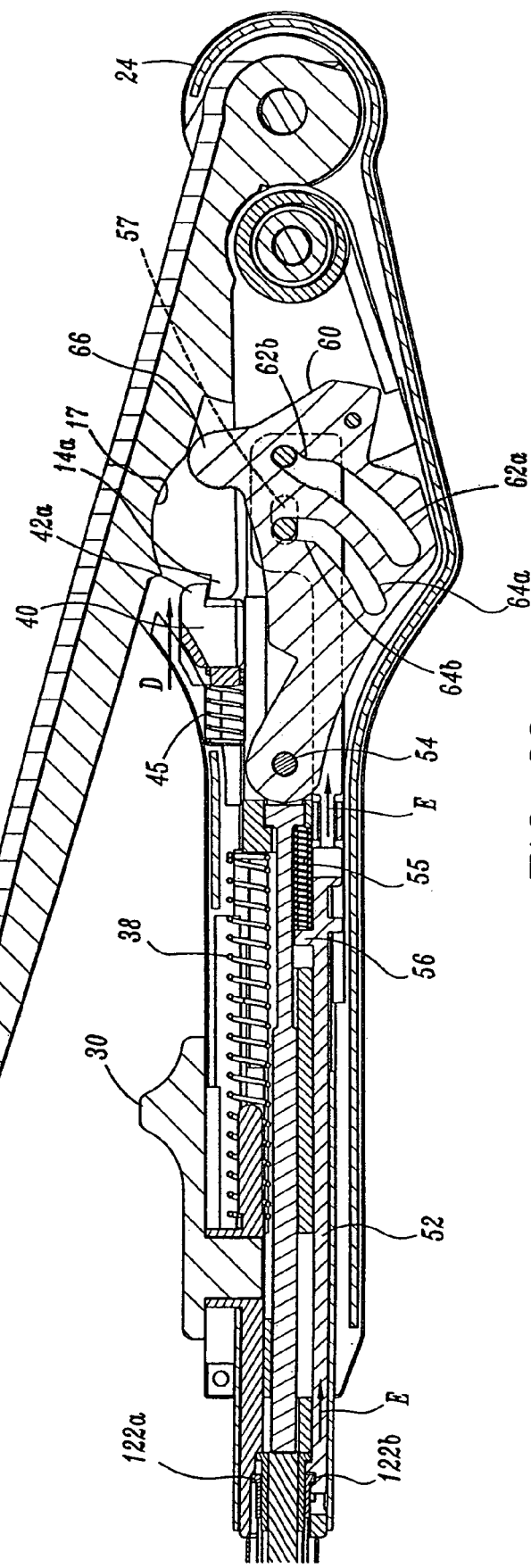
FIG. 21E
FIG. 22

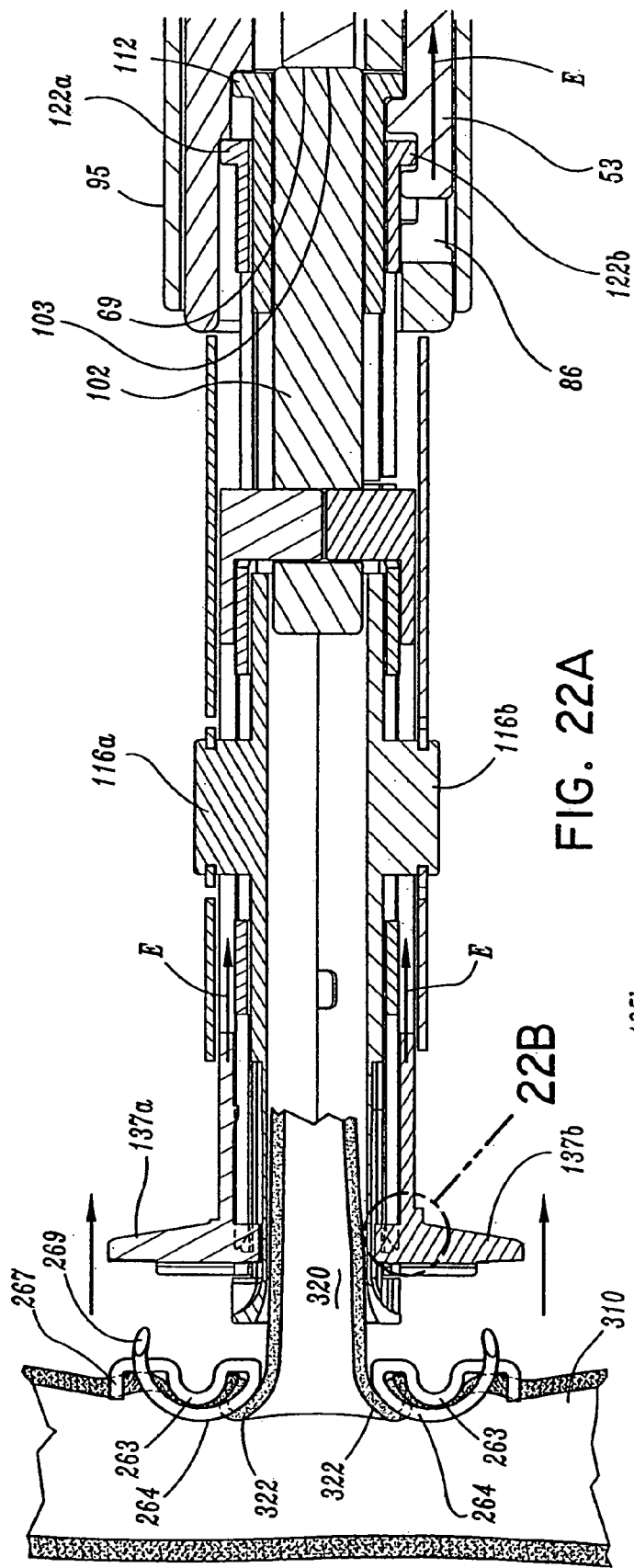
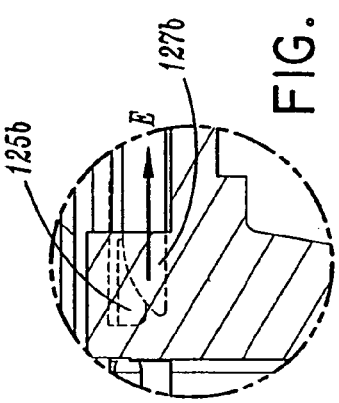
FIG. 22A
FIG. 22B

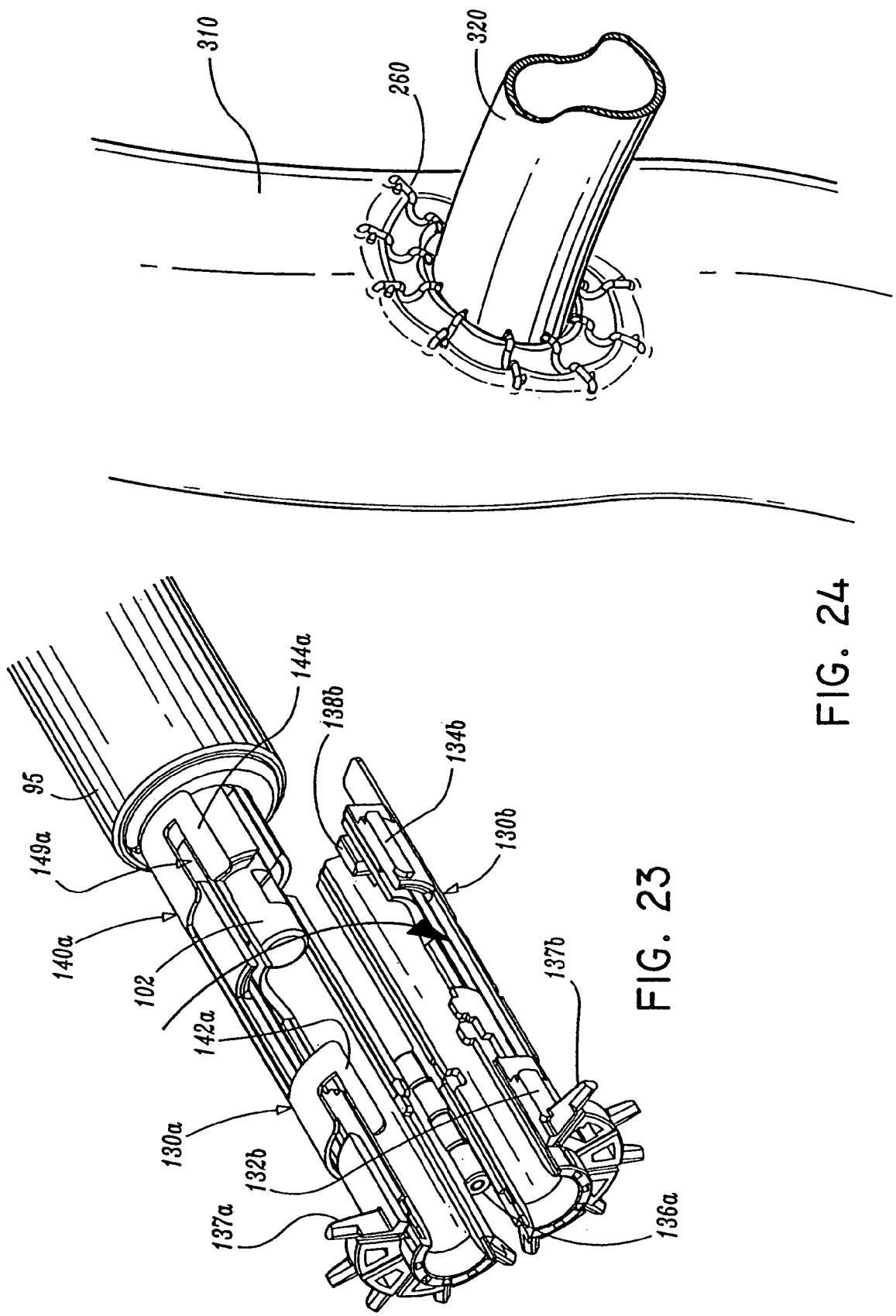

ANASTOMOSIS INSTRUMENT AND METHOD FOR PERFORMING SAME

CROSS REFERENCE TO RELATED APPLICATIONS

This application is a continuation of U.S. application Ser. No. 10/388,969 entitled "ANASTOMOSIS INSTRUMENT AND METHOD FOR PERFORMING SAME" which was filed on Mar. 13, 2003 by Milliman et al., now U.S. Pat. No. 7,204,843 which is a continuation of U.S. application Ser. No. 09/882,245 entitled "ANASTOMOSIS INSTRUMENT AND METHOD FOR PERFORMING SAME" which was filed on Jun. 14, 2001 by Milliman et al., now abandoned, which is a continuation of U.S. application Ser. No. 09/410,817, entitled "ANASTOMOSIS INSTRUMENT AND METHOD FOR PERFORMING SAME" which was filed on Oct. 1, 1999 by Milliman et al., now abandoned, which is a continuation-in-part of U.S. application Ser. No. 09/256,260, entitled "ANASTOMOSIS INSTRUMENT AND METHOD" which was filed on Feb. 23, 1999 by Nicholas et al., now U.S. Pat. No. 6,083,234, which is a continuation-in-part of U.S. application Ser. No. 08/877,701 entitled "SINGLESHOT ANASTOMOSIS INSTRUMENT WITH DETACHABLE LOADING UNIT AND METHOD", which was filed on Jun. 17, 1997 by Manzo et al., now U.S. Pat. No. 6,024,748, which is a continuation-in-part of U.S. application Ser. No. 08/685,385, entitled "ANASTOMOSIS INSTRUMENT AND METHOD", filed on Jul. 23, 1996 by Hinchliffe et al., now U.S. Pat. No. 5,707,380. U.S. application Ser. No. 09/256,260, now issued as U.S. Pat. No. 6,083,234, U.S. application Ser. No. 08/877,701, now issued as U.S. Pat. No. 6,024,748, as well as U.S. application Ser. No. 08/685,385, now issued as U.S. Pat. No. 5,707,380, are all herein incorporated by reference in their entirety.

BACKGROUND

1. Technical Field

The present disclosure relates to a surgical instrument and method for performing anastomosis of tubular body structures, and more particularly to an instrument for joining vascular tissues, for example, during coronary artery bypass graft procedures.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and/or by modifications in behavior and diet. In other cases, dilatation of coronary arteries may be achieved by such procedures as angioplasty, laser ablation, atherectomy, catheterization, and intravascular stents.

For certain patients, a coronary artery bypass graft ("CABG") is the preferred form of treatment to relieve symptoms and the graft often increases life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery ("saphenous vein") located in the thoracic cavity adjacent the sternum is likewise suitable for grafting to a coronary artery, such as the left anterior descending artery ("LAD").

The performance of a CABG procedure typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum to allow the two opposing halves of the rib cages to be spread apart to expose the internal organs of the thoracic cavity.

U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating "window". The retractor includes a rigid frame and a translation frame slideably connected to the rigid frame. Lower and upper blades are rotatably mounted to the rigid frame and the translation frame respectively. The "window" approach enables the surgeon to gain access through a smaller incision and with less displacement of the ribs, and consequently, less trauma to the patient.

Once access to the thoracic cavity has been achieved, surgery on the heart may be performed. Such procedures typically require that the heartbeat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta.

Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is a complicated procedure requiring that the desired vessels be properly located and accessed. The progression of the guide wires and catheters must be closely monitored to determine proper placement. Furthermore, the introduction of catheters form punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB) when performed through a thoracotomy (when performed through a sternotomy, the procedure is commonly called open coronary artery bypass (OP-CAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the saphenous vein, is grafted to the coronary artery by end-to-side anastomosis. Typically, sutures are used to graft the vessel segments. However, conventional suturing is complicated by the use of minimally invasive procedures, such as the window approach, e.g., limited access and reduced visibility to the surgical site may impede the surgeon's ability to manually apply sutures to a graft. Additionally, it is difficult and time consuming to manually suture if the CABG procedure is being performed while the heart is beating as the suturing must be synchronized with the heart beat.

As can be appreciated, the process of manually suturing the harvested vessel segment to a coronary artery is time consuming and requires a great deal of skill on the part of the surgeon. The resulting sutured anastomosis will also be dependent on the skills of the surgeon. In minimally invasive procedures such as in MIDCAB, the ability to suture is even more complicated due to limited maneuverability and reduced visibility. U.S. Pat. No. 5,707,380 to Hinchliffe et al., the entire contents of which are hereby incorporated by reference, discloses an apparatus and a procedure that enable remote anastomosis without piercing of vessels during both conventional and minimally invasive procedures. A continuing need exists, however, for improved surgical instruments and methods for performing remote anastomoses during both conventional and minimally invasive procedures.

SUMMARY

The present disclosure relates to a surgical instrument for anastomosis of first and second blood vessels which includes a housing having distal and proximal ends, a handle and a disposable loading unit removably mounted to the distal end of the housing. The disposable loading unit includes upper and lower fastener support members having a passage defined therethrough for receiving an end of the second blood vessel and configured to releasably support a plurality of surgical fasteners and a retractable anvil located at a distal end of the loading unit. The anvil is movable relative to the fastener support member in response to actuation of the handle to simultaneously deform the surgical fasteners.

In one embodiment, the loading unit includes two halves which are pivotable relative to one another to release the second vessel after the instrument is fired. Preferably, the fastener support member includes upper and lower fastener support members which support the fasteners in an array-like manner.

In another embodiment, the loading unit includes a first retracting sleeve which moves the anvil in response to actuation of the handle. Preferably, loading unit includes first and second retracting sleeves which are movable relative to the fastener support member from a first position wherein the distal ends of the retracting sleeves are disposed relative to the fastener support member to a second position wherein the distal ends of the retracting sleeves are disposed in closer proximity to the fastener support member.

In another embodiment, an actuator moves the first and second sleeves relative to the fastener support member. Preferably, continued movement of the handle moves the second sleeve relative to the first sleeve.

In another embodiment, the distal end of the first sleeve includes a plurality of elongated channels for supporting the surgical fasteners. Preferably, each of the channels includes a distal and proximal end wherein each distal end is radially offset from the proximal end such that the proximal and distal ends of the surgical fasteners are supported in a radially offset manner. It is envisioned that the second retracting sleeve releasably retains the surgical fasteners within the elongated channels and the anvil has an angled surface such that the distal ends of the surgical fasteners deform proximally upon actuation of the handle.

In another embodiment the actuator includes a cam having more than one cam follower. It is also envisioned that the cam may include multiple stages for imparting different, independent and/or varying movement to each of the cam followers upon actuation of the handle.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

An illustrative embodiment of the subject surgical instrument and method are described herein with reference to the drawings wherein:

FIG. 2 is an enlarged, partial perspective view of a single use loading unit (hereinafter "SULU") constructed in accordance with a preferred embodiment of the present disclosure;

FIG. 2A is an enlarged, perspective view of the indicated area of detail of FIG. 2;

FIG. 3 is a perspective view of a surgical fastener which is designed for operative engagement with the SULU for creating vascular anastomosis between two luminal vessels;

FIG. 4 is a side view the surgical instrument of FIG. 1;

FIG. 6 is a reverse, perspective view of the SULU of FIG. 2;

FIG. 6A is a reverse, perspective view of a lower half of the SULU of FIG. 2;

FIG. 7 is a perspective view with parts separated of the SULU of FIG. 2;

FIG. 7A is a greatly enlarged, perspective view of the indicated area of detail of FIG. 7;

FIG. 7B is a greatly enlarged, perspective view of the indicated area of detail of FIG. 7;

FIG. 7C is an enlarged, perspective view of a base portion of a first retracting sleeve;

FIG. 7D is a greatly enlarged, perspective view of the indicated area of detail of FIG. 7C;

FIG. 8 is a greatly enlarged, perspective view of the indicated area of detail of FIG. 7;

FIG. 9 is a greatly enlarged, perspective view of the indicated area of detail of FIG. 7;

FIG. 17 is a perspective view of the SULU with a first vessel inserted therethrough;

FIG. 18 is perspective of the SULU with an end of the first vessel everted over a distal end of the disposable unit being inserted into an incision in a second vessel;

FIG. 19 is an internal, perspective view of the second vessel with the SULU and the everted first vessel shown inserted therein;

FIG. 20 is a side cross-sectional view of the SULU and the everted first vessel shown inserted within the second vessel in pre-firing position;

FIG. 21B is a side cross-sectional view showing the movement of the SULU during the first firing stage to deform the surgical fasteners;

FIG. 21C is a greatly enlarged side cross-sectional view of the area indicated in detail in FIG. 21B;

FIG. 21D is a greatly enlarged perspective view of the surgical fastener shown in a "stapled" configuration;

FIG. 21E is a side view showing the relevant movement of a locking sleeve after the first firing stage;

FIG. 22 is a side cross-sectional view of the actuator assembly during the second firing stage and showing the internal movement of a second retractor within the actuator assembly;

FIG. 22A is a side cross-sectional view of the SULU during the second firing stage and showing the movement of a second retracting sleeve which moves as a direct result of the movement of the second retractor to release the surgical fasteners;

FIG. 22B is a greatly enlarged side cross-sectional view showing the retracting movement of a finger-like retention prong which moves as a direct result of the movement of the second retractor;

FIG. 23 is a perspective view of the SULU showing the pivotable movement of the two supports which open after firing to release the first vessel;

FIG. 24 is a view showing a completed anastomosis;

DETAILED DESCRIPTION OF PREFERRED EMBODIMENTS

Figure 1:
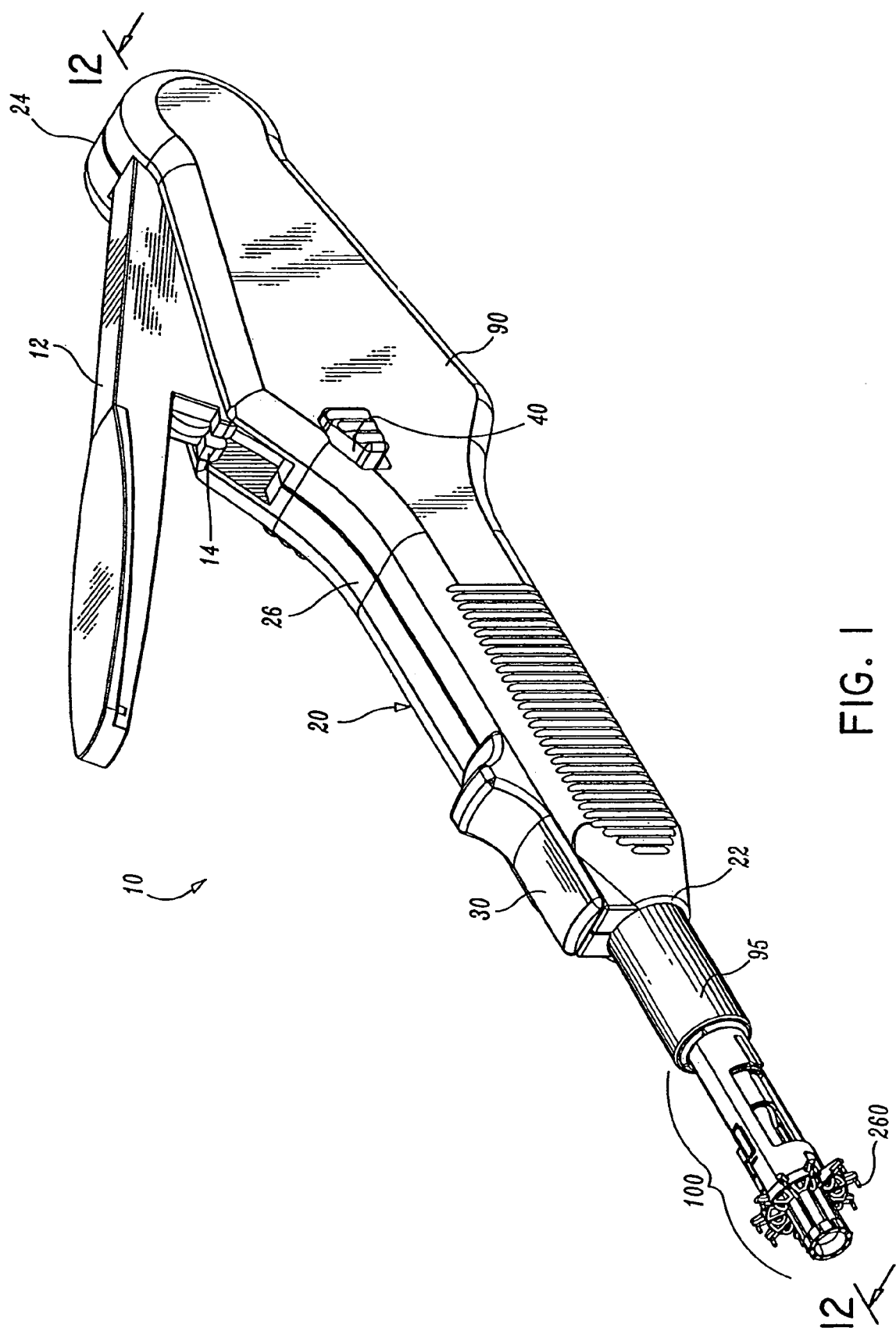
FIG. 1 is a perspective view of a surgical instrument constructed in accordance with a preferred embodiment of the present disclosure.
Figure 4A:
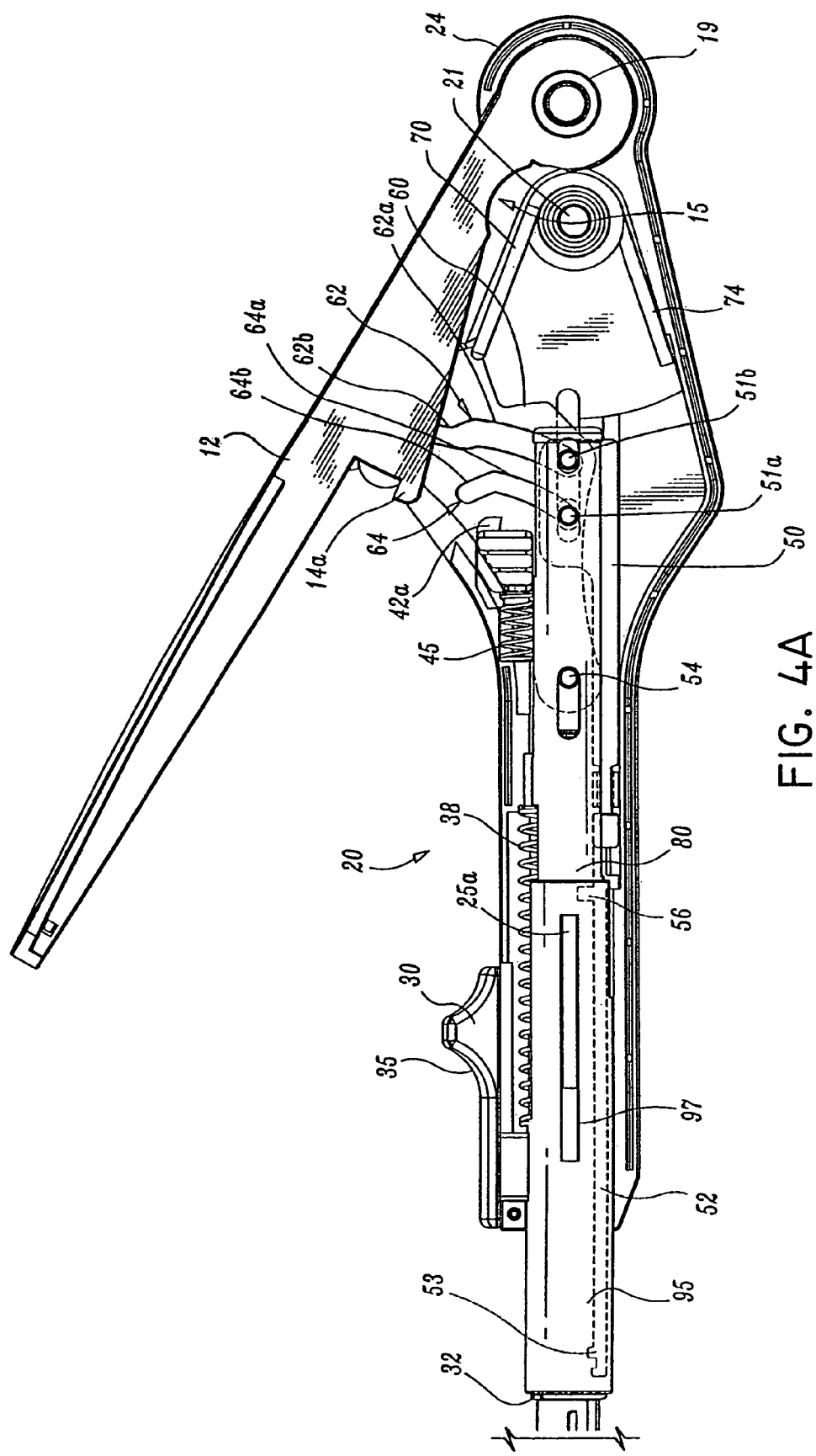
FIG. 4A is a left, side view of a handle/actuator assembly of the surgical instrument of FIG. 1 shown without a cover plate attached thereto.

Preferred embodiments of the surgical instrument and method disclosed herein will be described in terms of a coronary artery bypass procedure wherein a vascular anastomosis is created by joining a section of a harvested vessel, e.g., the saphenous vein, to bypass an occlusion in a coronary artery, e.g., the left anterior descending artery ("LAD") and/or aorta. Alternatively, the presently disclosed surgical instrument may also be utilized in performing anastomosis of other tubular luminal body structures.

In the drawings and in the description which follows, the term "proximal", as is traditional, will refer to the end of the apparatus which is closer to the user, while the term "distal" will refer to the end which is further from the user.

Referring now in detail to the drawing figures in which like reference numerals identify similar or identical elements, one embodiment of the present disclosure is illustrated generally in FIG. 1 and is designated therein as surgical instrument 10. Surgical instrument 10 includes two principal components, namely, an actuator assembly 20 and a disposable loading unit ("DLU") or a single use loading unit ("SULU") 100, which along with their internal working components, mechanically cooperate to deform a surgical fastener 260 to complete an anastomosis between two vessels, e.g., a saphenous vein 320 and an LAD and/or aorta 310 (FIG. 21B).

The particular surgical instrument 10 shown in the various figures is preferably designed to deform an array of surgical fasteners similar to fastener 260 shown in FIG. 3 which is generally L-shaped and includes a base leg 264 and an upwardly extending support leg 262. Preferably, base leg 264 includes a distal end 269 which is sufficiently shaped to penetrate the saphenous vein 320 and the LAD and/or aorta 310 upon deformation of the surgical fastener 260. The upwardly extending support leg 262 is attached to base leg 264 at a pivot point 265 and includes an inwardly extending prong 267 disposed at its free end designed to penetrate the LAD and/or aorta 310 and secure surgical fastener 260 in position after anastomosis. A convexity 263 projects inwardly between the base leg 264 and the support leg 262 and is preferably sufficiently dimensioned to cooperate with the base leg 264 to retain the saphenous vein 320 against LAD and/or aorta 310 in fluid communication after anastomosis as will be explained in greater detail below with respect to FIGS. 21B and 24. It is envisioned that the surgical fastener 260 can be arranged on the SULU in different patterns/arrays depending upon a particular purpose.

As best seen in FIGS. 1, 4, 10 and 11, actuator assembly 20 includes a proximal end 24, a distal end 22 and a housing 26 defined therebetween for storing the internal working components of the actuator assembly 20. Preferably, a plate 90 covers the internal components of the actuator assembly 20 when assembled. More particularly, housing 26 includes at least one mechanical interface 23a which reciprocates with a corresponding mechanical interface 23b (FIG. 10) disposed on cover plate 90 to matingly engage the two components 26 and 90.

Actuator assembly 20 also includes a handle 12 which initiates firing of the surgical instrument 10 and a spring-loaded thumb tab 30 for loading the SULU 100 onto the actuator assembly 20 both of which will be explained in greater detail below. Preferably, handle 12 is provided with an ergonomic surface which is contoured and configured to be comfortably gripped by the hand of the user during operation of the instrument.

Figure 11:
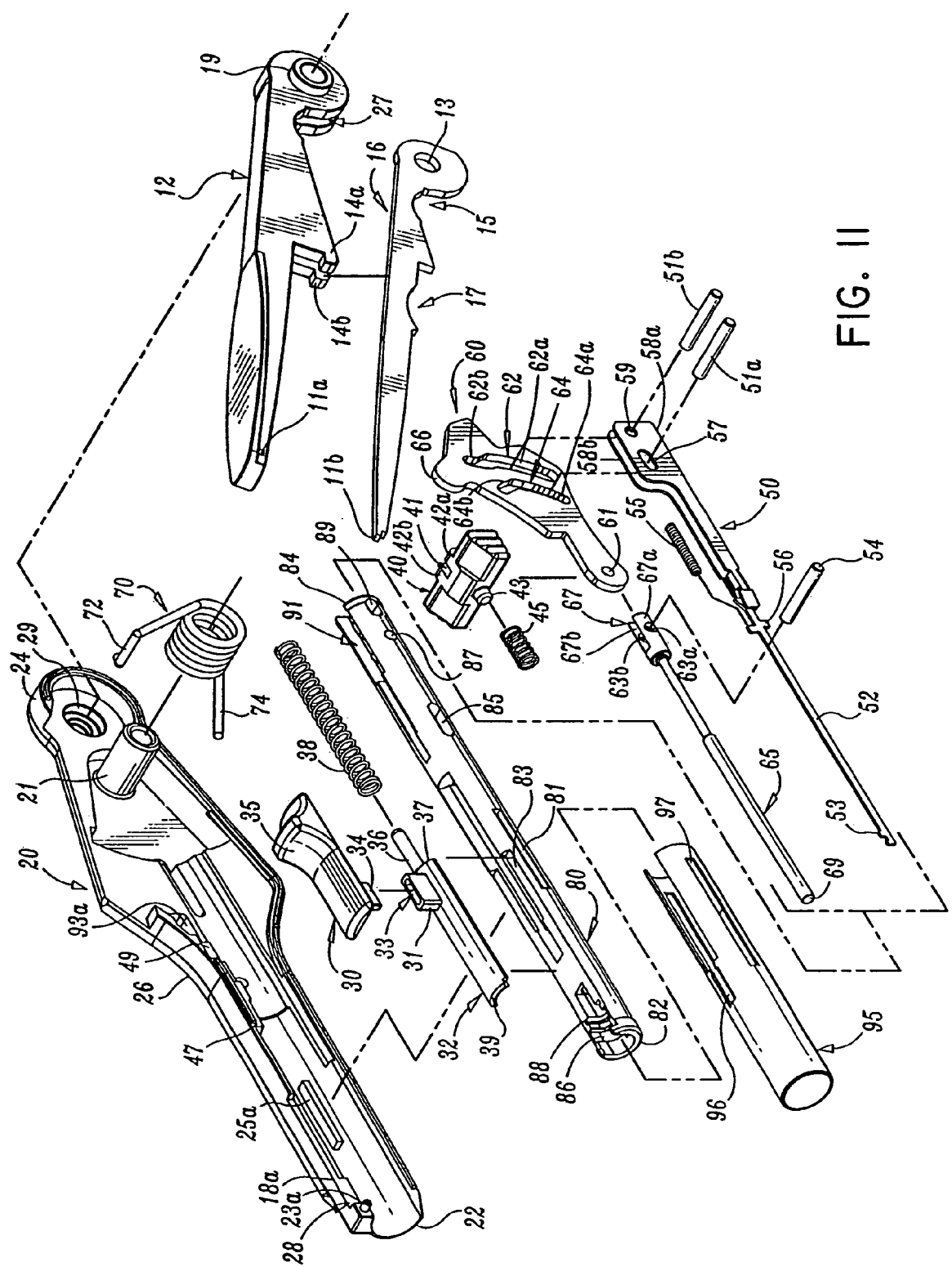
FIG. 11 is a perspective view the actuator assembly of FIG. 10 shown with parts separated.

Turning now to FIG. 11 which illustrates in detail the internal working components of the actuating assembly 20 which are preferably assembled and stored within housing 26. More particularly, the actuating assembly 20 includes a torsion spring 70 which mounts about post 21 which protrudes from housing 26. Spring 70 includes a lower arm 74 which is biased against a lower portion of the housing and an upper arm 72 which is biased against a rotating two-stage cam 60.

Handle 12 includes a bushing 19 which protrudes laterally from the proximal end of the handle 12 and pivotally engages a corresponding recess 29 disposed within the proximal end 24 of housing 26 to allow pivotal movement of the handle 12 with respect to housing 26. Handle 12 also includes a vertically extending slot 27 disposed at its proximal end 24 which receives the proximal end of a lever 16 which moves in conjunction with the handle 12. A pair of flanges 14a and 14b downwardly extend from the handle 12 and receive lever 16 therebetween. A mechanical interface 11a disposed on handle 12 engages a corresponding mechanical interface 11b disposed on lever 16 to secure the lever 16 to the handle 12. Preferably, lever 16 has a first recess 17 shaped to engage and control the movement of the cam 60 during downward movement of the handle 12, the purpose of which will be explained in more detail with respect to FIG. 21A. Lever 16 also includes a second recess 15 which helps to limit lateral movement of the spring 70 within housing 26.

Figure 10:
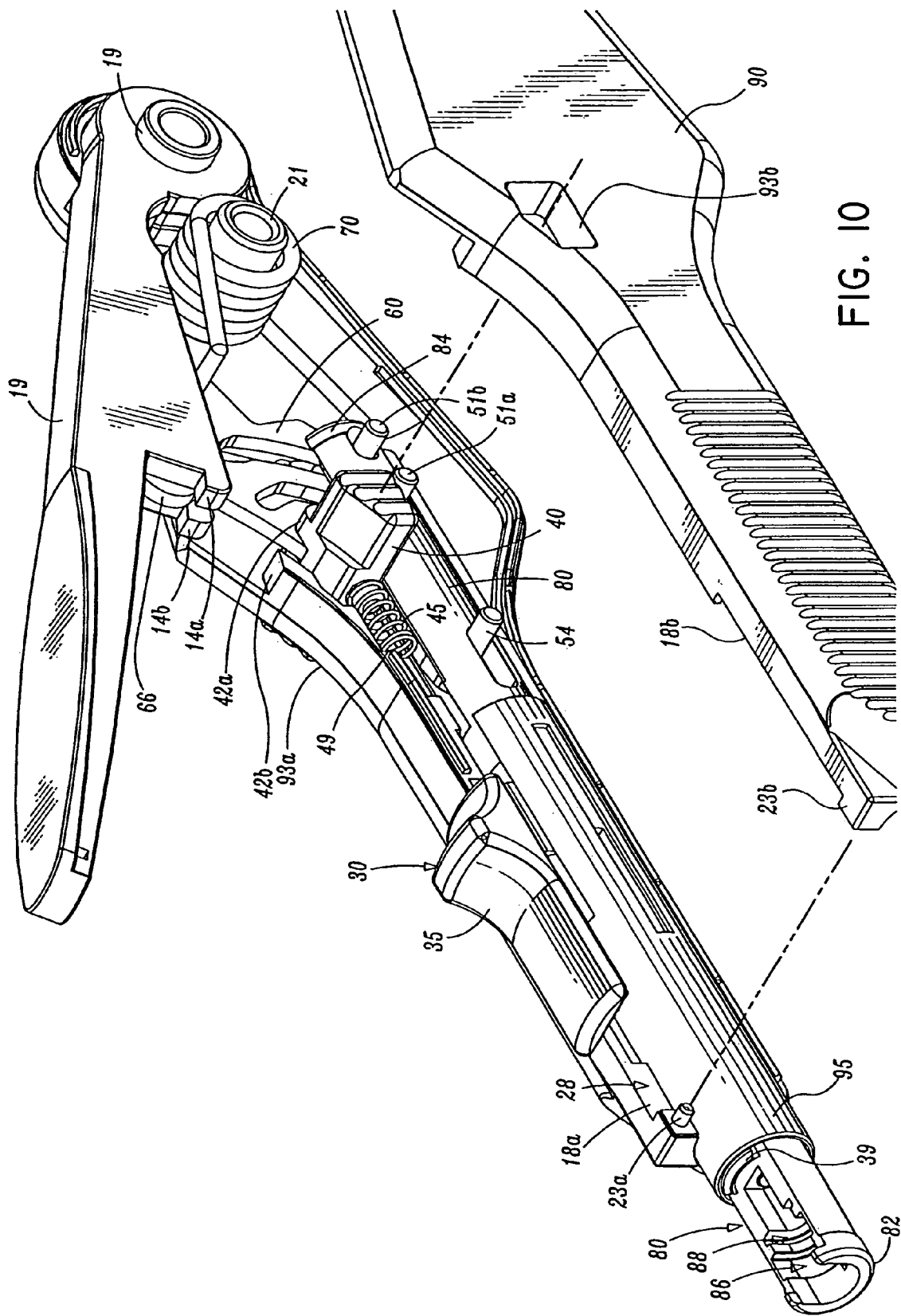
FIG. 10 is a perspective view of the actuator assembly with the cover plate shown separated.

As mentioned above, actuating assembly 20 also includes a spring-loaded thumb tab 30 which rests atop housing 26 within a longitudinally extending slot 28 disposed near the distal end 22 thereof. As best seen in FIG. 10, slot 28 is formed by notches 18a and 18b of the housing 26 and cover plate 90, respectively. Tab 30 includes a thumb guide 35 which cooperates with a sliding sleeve 32 to facilitate proximal movement of the tab 30 for loading the SULU. A downwardly depending flange 34 disposed on tab 30 engages a corresponding slot 33 located in a mount 31 disposed atop the sliding sleeve 32. Preferably, sliding sleeve 32 includes a post 36 which is dimensioned to receive a tension spring 38 thereon. Spring 38 is biased between a block 47 disposed within housing 26 and a proximal edge 37 of sliding sleeve 32 such that spring 38 biases sliding sleeve 32 to a distal-most position proximate distal end 22. Preferably, a distal end 39 of sleeve 32 is arcuate or semi-circular and is dimensioned to slidingly engage a corresponding end 82 of a first retractor 80 to lock the SULU 100 within the actuator assembly 20 after the SULU 100 is loaded as will be discussed in more detail below.

Actuator assembly 20 also includes first retractor 80 and a second retractor 50 which each move by way of movement of the handle 12 which, in turn, imparts movement to the two-stage cam 60. First retractor 80 includes distal and proximal ends 82 and 84, respectively, and is generally tubular in dimension with the exception of an elongated furrow 83 extending proximally from distal end 82 for slidingly supporting sleeve 32. Retractor 80 also includes a slot 85 for receiving a pin 54 for affixing the retractor 80 to the cam 60 and another pair of slots 87 and 89 located near the proximal end 84 for receiving two cam followers 51a and 51b, respectively. Preferably, the proximal end 84 is bifurcated to facilitate insertion of the second retractor 50 therein.

Figure 16:
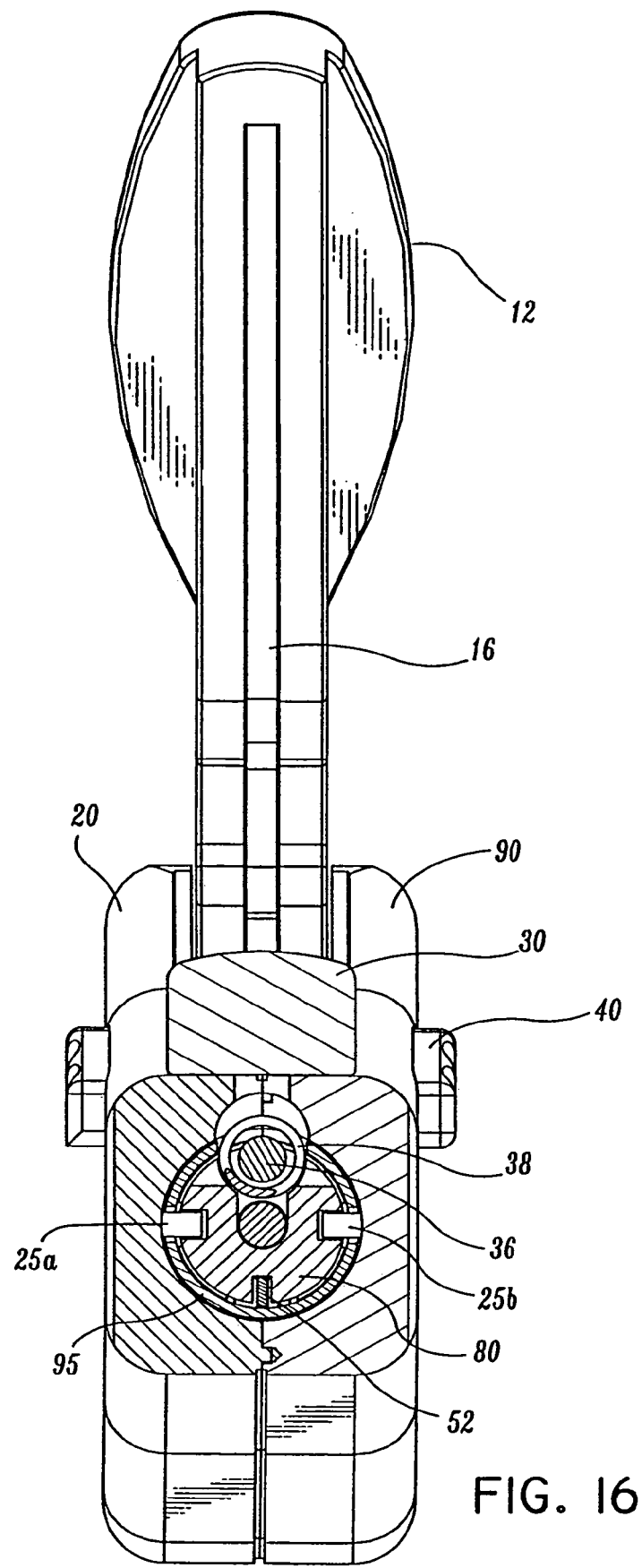
FIG. 16 is a front cross-sectional view of the surgical instrument taken along section line 16-16 of FIG. 12.

As best seen in FIGS. 11 and 16, a guide 81 engages an elongated rib 25a in housing 26 and an elongated rib 25b in cover plate 90 to slidingly mount the retractor 80 to housing 26. Guide 81 is dimensioned slightly longer than rib 25a to permit proximal movement of the first retractor 80 relative to the housing 26 upon activation of the handle 12. Preferably, a protective tube 95 is telescopically disposed about the first retractor 80 and moves in conjunction with the sliding sleeve 32 by way of slot 96 which secures mount 31 of the sliding sleeve 32 therein. It is anticipated that protective tube 95 also helps to restrict lateral movement of the first retractor 80 during retraction. Tube 95 also includes an elongated channel 97 which generally aligns with guide 81 located in the first retractor 80 to mount both components to ribs 25a and 25b.

Figure 5:
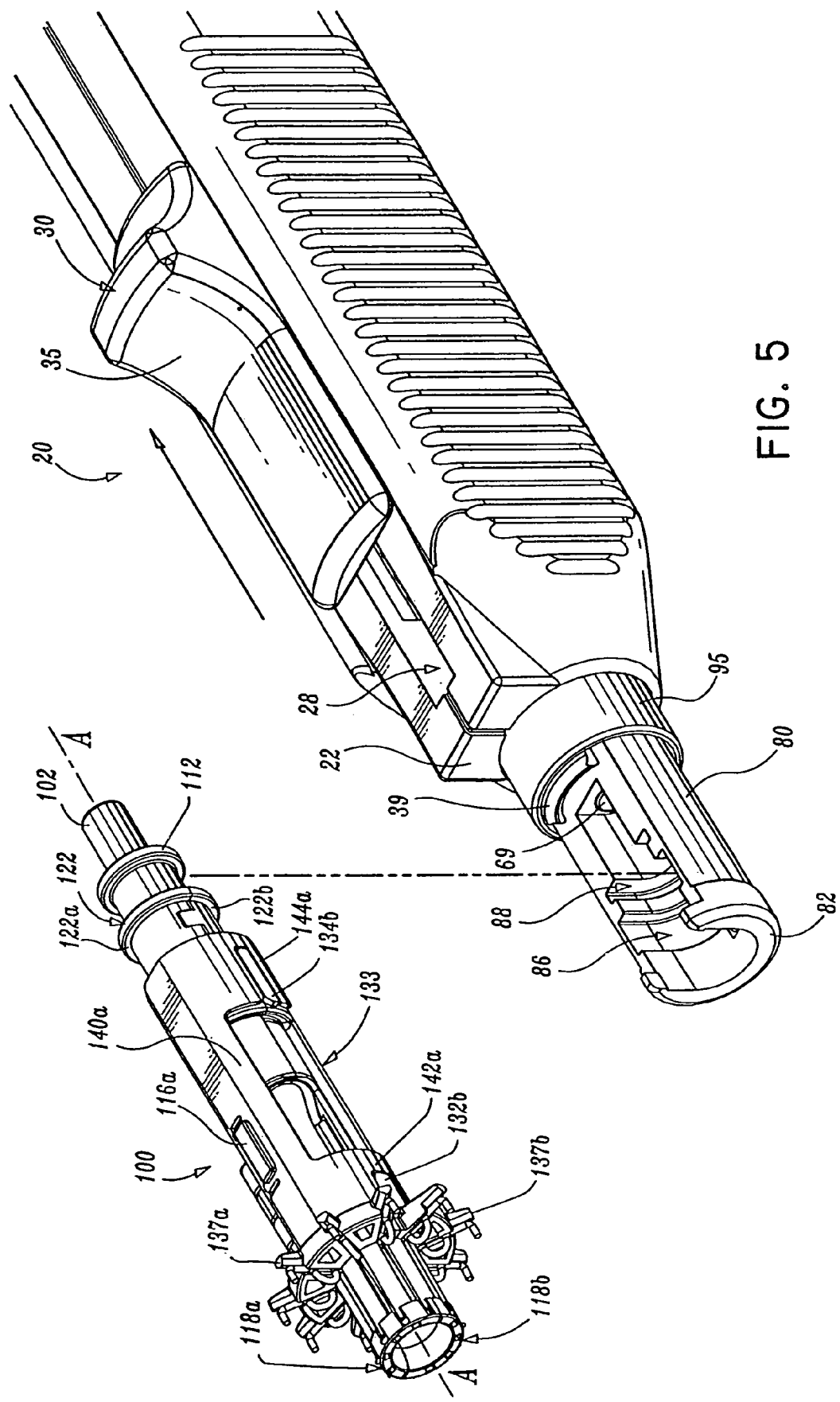
FIG. 5 is an enlarged, perspective view of a distal end of the actuator assembly shown in a pre-loading position to receivingly engage the SULU.

It is contemplated that proximal movement of tab 30 will impart reciprocating proximal movement to the sliding sleeve 32 to expose carriages 86 and 88 disposed within the first retractor 80 which are designed to receive a pair of first and second retracting sleeves 110 and 120 (FIGS. 7-9) of the SULU 100. More particularly, and as best seen in FIG. 5, carriage 86 is generally circular in shape and is designed to receive an outer lip 122 formed by the union of end 122a and 122b of second retracting sleeve 120 of the SULU 100. Preferably, carriage 86 is dimensioned larger that the lip 122 so as to permit proximal movement of the second retracting sleeve 120 relative to the first retracting sleeve 110 as will be explained in more detail with respect to FIG. 22A. Carriage 88 is likewise circular in shape and receives outer lip 112 of the first retracting sleeve 110.

Figure 12:
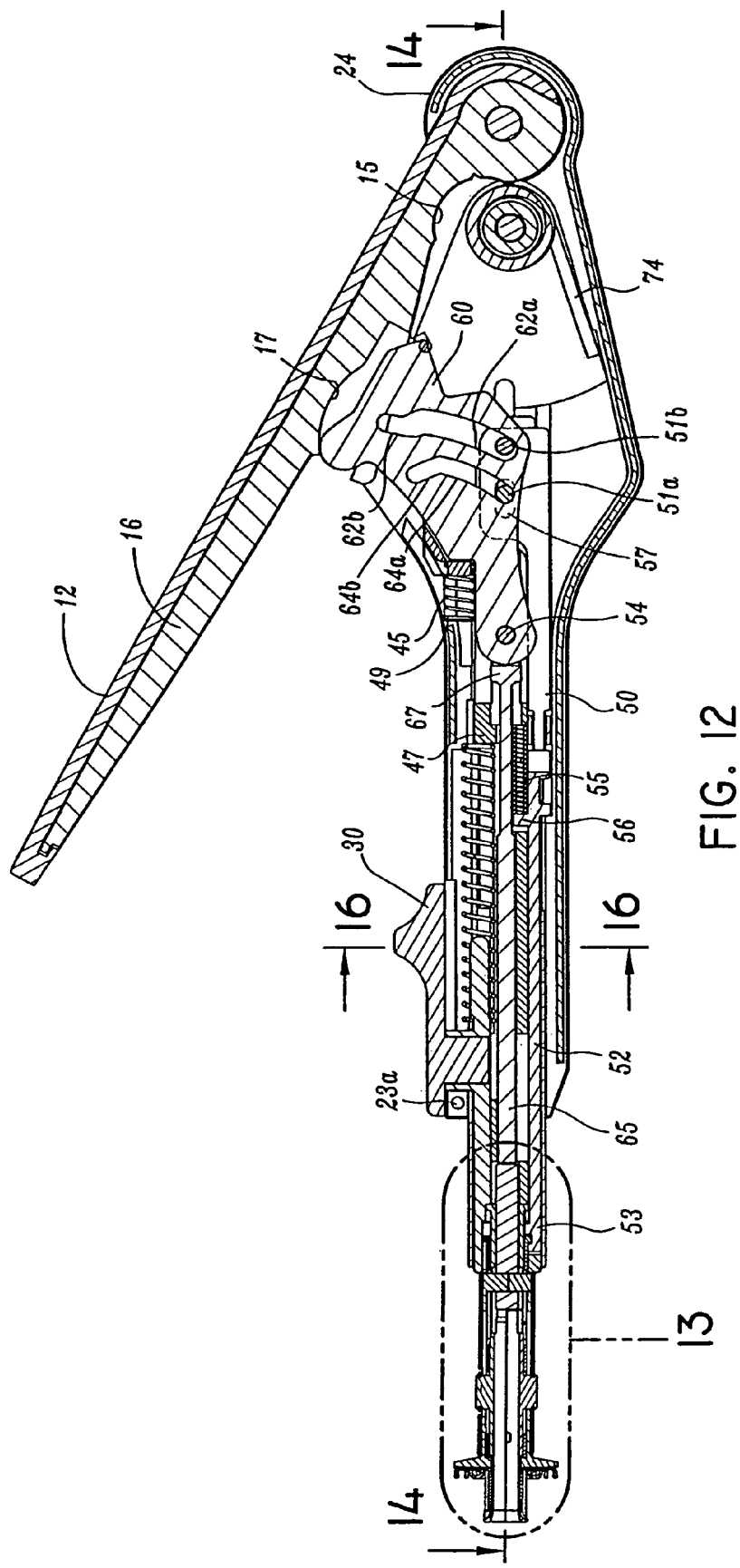
FIG. 12 is a horizontal cross-sectional view of the surgical instrument of FIG. 1 shown loaded for firing.

Actuator assembly 20 also includes a handle lock 40 which rests atop the first retractor 80 and extends laterally between the housing 26 and the cover plate 90. More particularly, handle lock 40 is mounted within slots 93a and 93b as best seen in FIG. 10. Handle lock 40 includes a post 43 which receives a spring 45 for biasing handle lock 40 against a ledge 49 of the housing 26 (FIG. 12). Handle lock 40 also includes a pair of flanges 42a and 42b which align with flanges 14a and 14b disposed on handle 12. As shown best in FIGS. 21 and 22, downward movement of the handle 12 forces the handle lock 40 initially distally against spring 45 until flanges 14a and 14b clear flanges 42a and 42b at which point spring 45 forces handle lock 40 proximally to lock flanges 42a and 42b atop flanges 14a and 14b and to lock handle 12 in a downwardly disposed position. Preferably, flanges 42a and 42b define a slot 41 for receiving lever 16 therebetween.

Actuator assembly 20 also includes a second retractor 50 which includes an elongated arm 52 having a key-like distal end 53 and a T-shaped heel section 56. Preferably, T-shaped heel section 56 attaches to a tension spring 55 disposed proximally thereof. Second retractor 50 is preferably bifurcated at its proximal end forming two longitudinally extending fins 58a and 58b each having a slot 57 and aperture 59 for receiving cam followers 51a and 51b, respectively. It is contemplated that spring 55 is biased against an elongated stop 65 which rests atop arm 52 and biases heel section 56 proximally when the second retractor 50 is retracted which will be explained in more detail below with respect to the operation of the surgical instrument 10.

As mentioned above, the first retractor 80 is affixed to two-stage cam 60 by pin 54. More particularly, cam 60 includes an aperture 61 located near the distal end thereof for receiving pin 54 which affixes the cam 60 to the first retractor 80. Cam 60 also includes a pair of generally vertical arcuately-shaped slots 62 and 64 which each include two discrete stages, namely 62a, 62b and 64a, 64b, respectively, for imparting movement to corresponding followers 51a and 51b. A nub 66 is located near the uppermost portion of the cam 60 and is dimensioned to slideably engage recess 17 located in lever 16 as best illustrated in FIG. 12.

Figure 21:
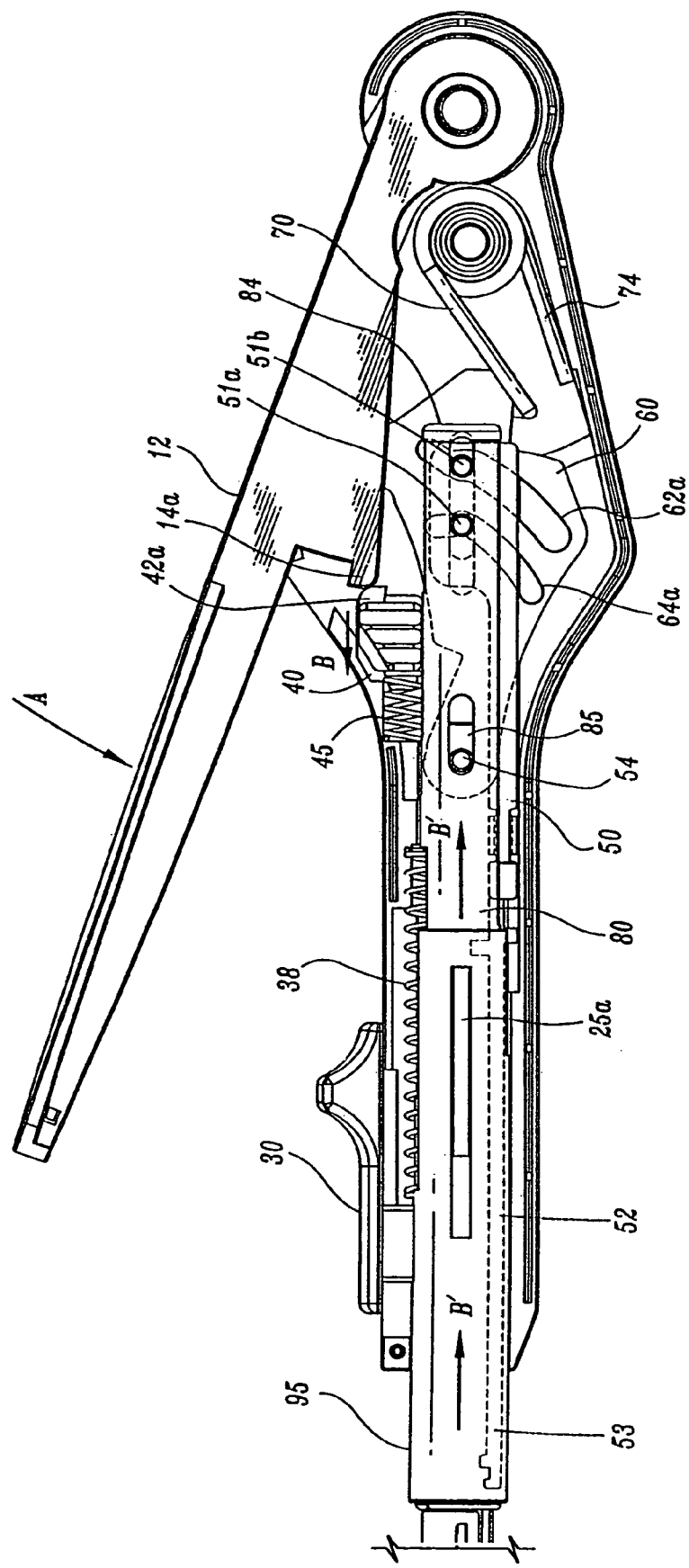
FIG. 21 is a side view of the actuator assembly without the cover plate during a first firing stage of the instrument and showing the internal movement of a first retractor within the actuator assembly.
Figure 21A:
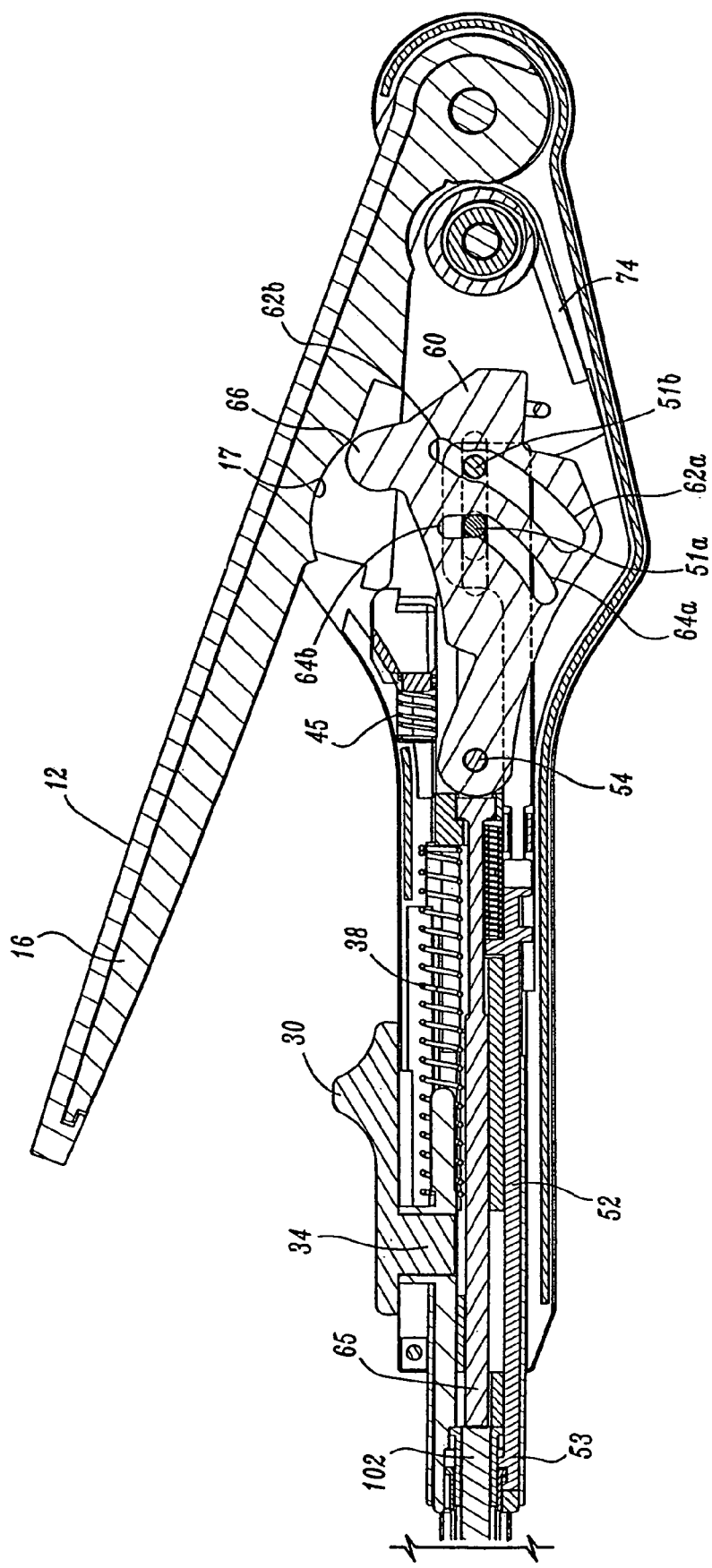
FIG. 21A is a side cross-sectional view showing the relevant positions of the internal working components of the actuator assembly after the first firing stage.

It is contemplated that during downward movement of handle 12, lever 16 will bias nub 66 downwardly such that nub 66 rides proximally along recess 17 and causes cam 60 to pivot downwardly about pin 54 as shown best in FIGS. 21A and 22. In turn, followers 51a and 51b will ride along slots 64 and 62 and cause the first and second retractors 80 and 50 to move in a proximal direction which will be explained in more detail below. Preferably, recess 17, nub 66 and slots 64 and 62 can be dimensioned to control the movement and timing of the cam followers 51a and 51b. For example, it is envisioned that the stages 64a, 64b and 62a and 62b can be dimensioned to control the timing and movement of the first and second retractors which, in turn, can effect the efficiency of the anastomosis.

Elongated stop 65 is preferably affixed to the distal end of cam 60 and rests atop the second retractor 50. Elongated stop 65 includes a distal end 69 and a proximal end 67 which includes two extending portions 67a and 67b each having an aperture 63a and 63b, respectively, disposed therethrough. Preferably, end 69 of stop 65 is sufficiently dimensioned such that it engages a corresponding biasing post 102 located within the SULU 100.

Preferably, the second retractor 50, the cam 60 and the elongated stop 65 are pre-assembled prior to insertion into the first retractor 80. More particularly and as best illustrated in FIGS. 10-12, elongated stop 65 is positioned atop arm 52 of the second retractor 50 between T-shaped heel section 56 and end 53. Apertures 63a and 63b of stop 65 align with aperture 61 of cam 60 such that once the cam 60 and the elongated stop 65 are inserted within slot 91 of the first retractor 80, pin 54 locks the two components 65 and 60 together through slot 85.

Cam 60 is positioned between the extending fins 58a and 58b of the second retractor 50 such that, when the retractor 50 and cam 60 are inserted within slot 91 of the first retractor, followers 51a and 51b are inserted through slot 87 and slot 89, respectively, and slideably couple the two components 50 and 60 within the first retractor 80. Handle lock 40 is then positioned atop the first retractor 80 as described above. First retractor 80 is then mounted on ribs 25a and 25b of housing 26 and cover plate 90, respectively and tab 30 along with sliding sleeve 32 are engaged thereon. Handle 12 and lever 16 are then assembled as described above and pivotably mounted about post 21. Spring 70 is then positioned accordingly so as to bias handle 12 against housing 26.

Turning now to FIGS. 7-9 which show an exploded view of the internal working components of the SULU 100 which as mentioned above includes first retracting sleeve 110 and second retracting sleeve 120 which cooperate to deform fasteners 260 and securely fasten the saphenous vein 320 to the LAD and/or aorta 310 in fluid communication as shown in FIG. 24.

More particularly and as best seen in FIGS. 7-7D, first retracting sleeve 110 includes a tube-like base 110a and an arcuate sleeve cap 110b which together define the first retracting sleeve 110. Base 110a includes a circular lip 112 located at its proximal end and a semi-circular anvil 118a located at the opposite end. A locking tab 116a having an elongated slit 182a located therein is disposed between lip 112 and anvil 118a. A longitudinally-extending slot 114a is disposed between the lip 112 and the locking tab 116a. At least one interface 117a downwardly depends from base 110a to mechanically engage a corresponding mechanical interface 117b disposed on sleeve cap 110b (FIG. 7). A flange 113a is preferably disposed beneath slot 114a and is sufficiently dimensioned to engage corresponding flanges $113b_1$ and $113b_2$ located on sleeve cap 110b. Slot 114a is sufficiently dimensioned to receive a tab 138a (FIG. 13) which projects from an upper surgical fastener support 130a which is explained in more detail below.

Sleeve cap 110b includes a semi-circular anvil 118b and a bifurcated proximal end 113 composed of flanges $113b_1$ and $113b_2$ which together define a slot 114b for receiving a tab 138b which projects from a lower surgical fastener support 130b which is explained in more detail below. Sleeve cap 110b also includes mechanical interfaces 117b which couples with corresponding mechanical interfaces 117a disposed on base 110a to engage sleeve cap 110b with base 110a. A locking tab 116b having an elongated slit 182b located therein is disposed between proximal end 113 and anvil 118b. A longitudinally-extending opening 111b is preferably disposed proximate locking tab 116b and aligns with a corresponding opening 111a in base 110a (FIG. 7C) such that the saphenous vein 320 can be received therethrough as seen best in FIGS. 17 and 18.

Figure 13:
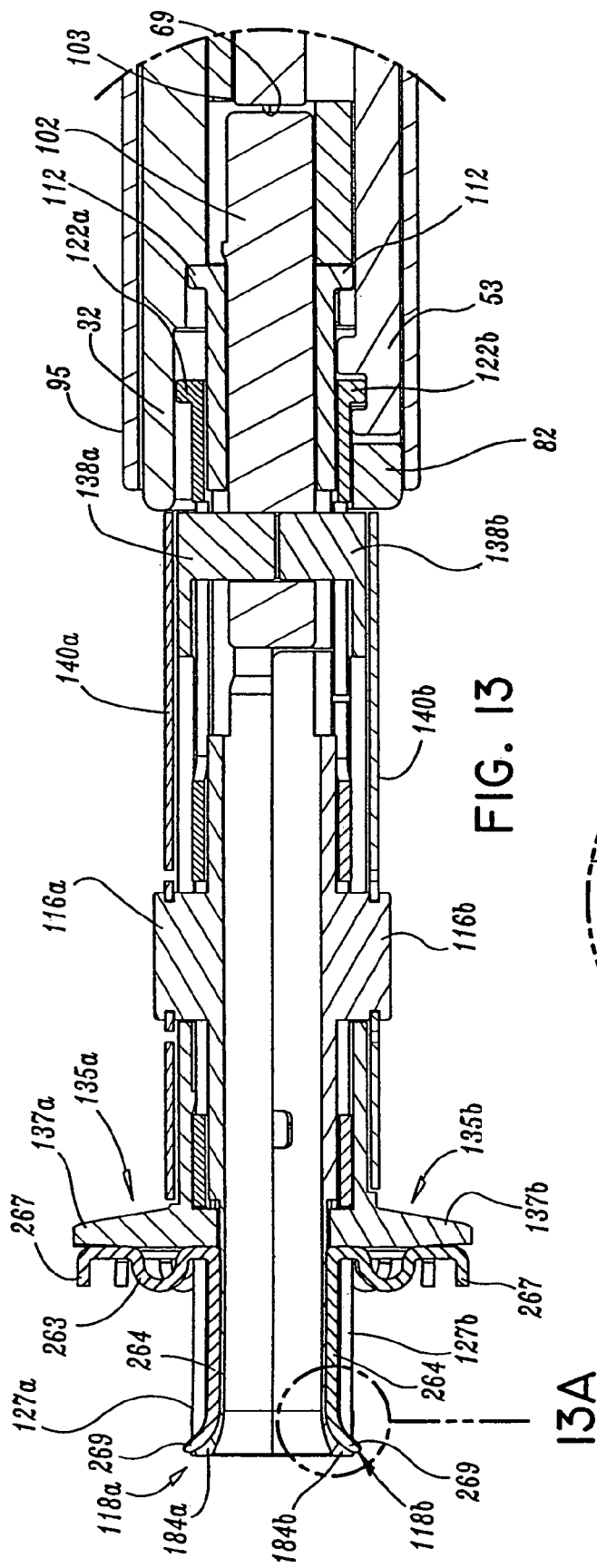
FIG. 13 is a horizontal cross-sectional view of the indicated area of detail of FIG. 12.
Figure 13A:
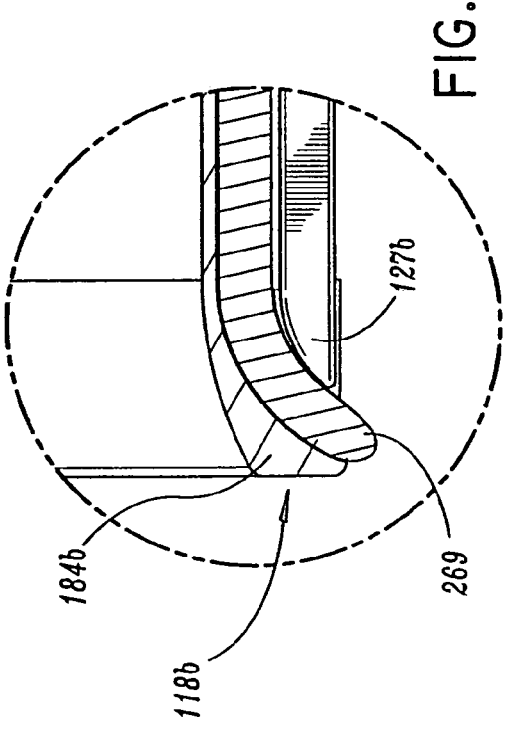
FIG. 13A is a greatly enlarged horizontal cross sectional view of the area indicated in detail of FIG. 13.
Figure 14:
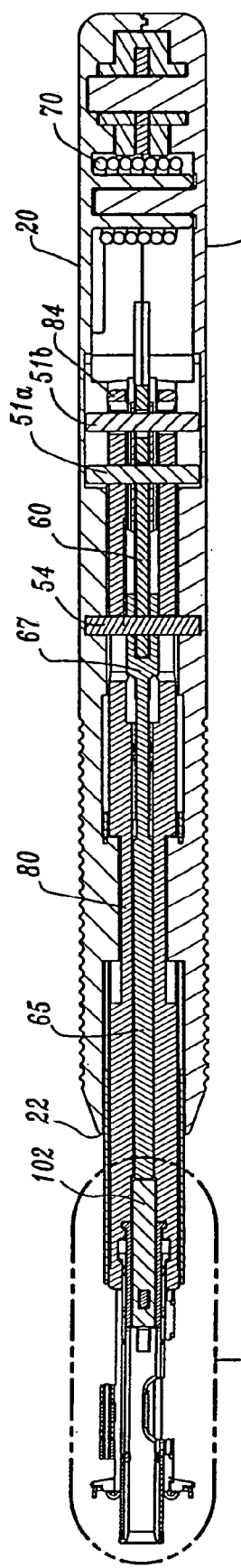
FIG. 14 is a top cross-sectional view of the surgical instrument taken along section line 14-14 of FIG. 12.
Figure 15:
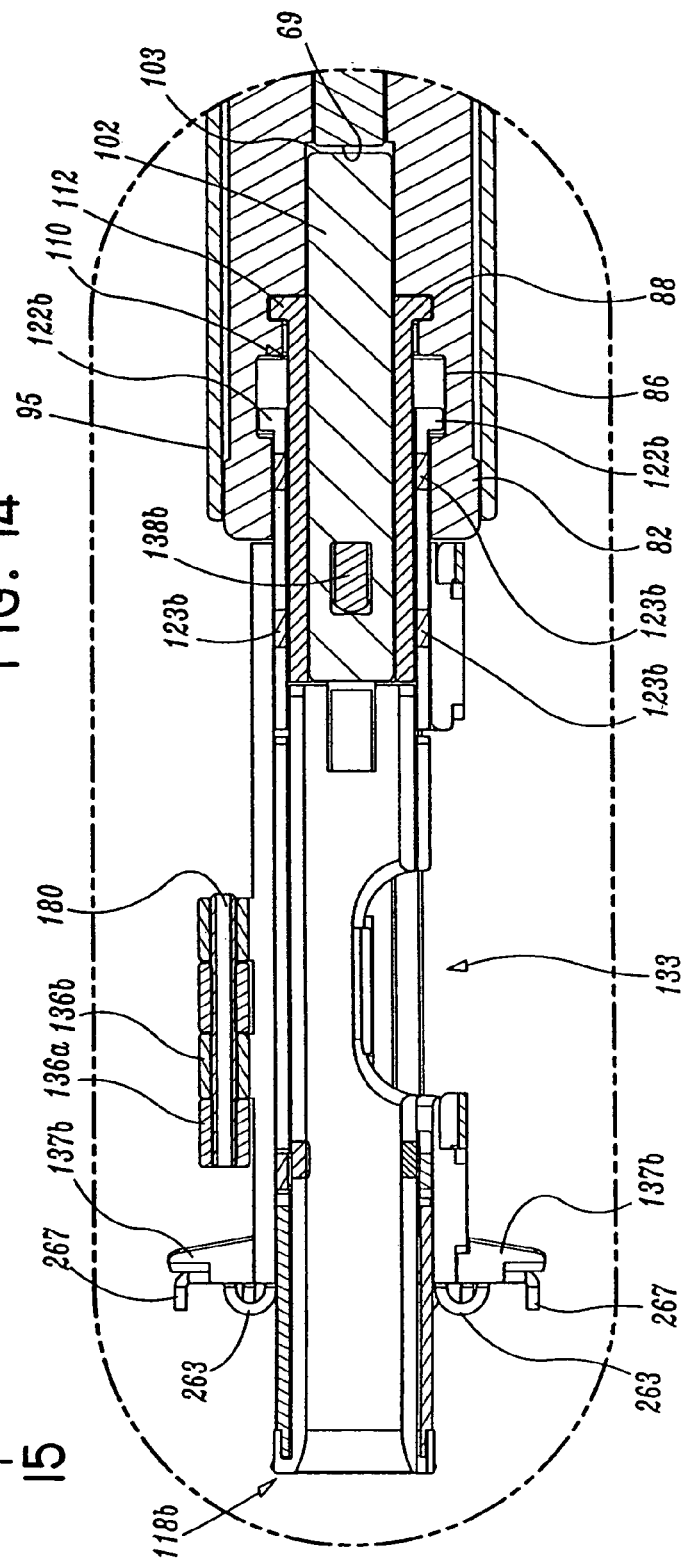
FIG. 15 is a greatly enlarged top cross-sectional view of the area indicated in detail of FIG. 14.

FIGS. 2A and 7D show a greatly enlarged view of anvil 118a which includes a semi-annular array of fastener support channels or cradles 119a each configured and dimensioned to support a surgical fastener 260 therein. Sleeve cap 110b also includes fastener support channels 119b which, when base 110a and sleeve cap 110b are assembled, align to form a circular array about the internal surfaces of anvil 118a and 118b. It is envisioned that anvils 118a and 118b can be designed to support different arrays of surgical fasteners 260 depending upon a particular purpose. Each channel 119a and 119b is preferably separated by an anchor 187a and 187b (FIG. 7) which releasably retains a projecting finger 124a, 124b of second retracting sleeve 120 (FIG. 2A). Support channels 119a and 119b each include proximal ends 186a and 186b and distal ends 184a and 184b which are radially offset from one another to seat surgical fastener 260 within channels 119a and 119b in a radially offset manner the purpose of which will be explained below with respect to the operation of the surgical instrument 10. The distal end 184a of each channel 119a is preferably arched so as to correspond to the arcuate shape of the end of the surgical fastener 260 as best seen in FIG. 13A. It is anticipated that arching the distal end 184a will cause the surgical fastener 260 to deform upwardly and proximally upon retraction of the first retracting sleeve 110 by the first retractor 80 as explained below with reference to FIGS. 21-22.

FIGS. 7-7D also show second retracting sleeve 120 which includes an upper cuff 120a, a lower cuff 120b and an outer cap 128 which together define the second retracting sleeve 120. More particularly, upper cuff 120a includes a semi-annular lip 122a at one end and a plurality of retention fingers 124a at the opposite end. Upper cuff 120a also includes a first slot 101 which preferably aligns with slot 114a of the first retracting sleeve 110a to receive tab 138a of upper fastener support 130b therethrough (FIG. 20). A second slot 126a receives locking tab 116a when cuff 120a is slideably mounted atop base 110a. Interfaces 129a mechanically engage corresponding interfaces 129b located on lower cuff 120b.

Lower cuff 120b includes a bifurcated proximal end 107 which comprises flanges $107b_1$ and $107b_2$ which define a slot 108 for receiving tab 138b of lower fastener support 130b therethrough and a plurality of retention fingers 124b which extend from the opposite end thereof. A slot 126b is disposed between the flanges $107b_1$, $107b_2$ and the fingers 124b for receiving locking tab 116b of the sleeve cap 110b when cuff 120b is slideably mounted thereon. A longitudinally-extending opening 121b is disposed proximate slot 126b and aligns with a corresponding opening 121a in upper cuff 120a and also aligns with openings 111a and 111b of the first retracting sleeve 110 such that the saphenous vein 320 can be received therethrough as seen best in FIGS. 17 and 18.

A semi-circular cuff cap 128 is disposed atop lower cuff 120b and mechanically interfaces with upper cuff 120a such that semi-circular lips 122a and 122b for circular lip 122. More particularly, cuff cap 128 includes a plurality of detents 123b which mechanically engage a corresponding plurality of notches 123a located in upper cuff 120a such that the cuff cap 128, upper cuff 120a and lower cuff 120b all move in unison upon retraction of the second retracting sleeve 120. Sleeve cap 128 is preferably bifurcated at its distal end forming slot 109 which is dimensioned to receive tab 138b.

As can be appreciated, fingers 124a and 124b move upon retraction of the second retracting sleeve 120 to release the surgical fasteners 260 after firing. More particularly and as best seen in FIGS. 2A and 7A, the distal end of each finger 124a is forked and includes a first prong 127a which retains a surgical fastener 260 within the fastener support channels 119a and a second prong 125a which interlocks with anchor 187a to releasably lock the finger 124a to the first retracting sleeve 110 until released by the second retractor 50 (FIGS. 22A and 22B) which will be explained in more detail with respect to the operation of the surgical instrument 10. Likewise, each finger 124b of lower cuff 120b includes prongs 127b and 125b which operates in the same manner.

As mentioned previously, the SULU 100 also includes fastener support 130 which has an upper support 130a and a lower support 130b which, when assembled, internally house the first and second retracting sleeves 110 and 120, respectively, along with their individual working components. Upper support 130a and lower support 130b each include a distal end 135a and 135b each having an array of braces 137a and 137b, respectively, which project radially from distal ends 135a and 135b. As best illustrated in FIG. 2, each brace 137a and 137b supports an upwardly extending support leg 262 of a surgical fastener 260 disposed within one of the channels 119a or 119b. A plurality of radially extending slots 139a and 139b are disposed between each support brace 137a, 137b for retaining a surgical fastener 260 therein and for restricting unwanted lateral movement of each fastener 260. It is anticipated that each surgical fastener 260 is positioned within a slot 139a, 139b such that convexity 263 projects outwardly from brace 137a, 137b and, after anastomosis, cooperates with the base leg 264 to retain the saphenous vein 320 against LAD and/or aorta 310 (FIGS. 21B and 24).

Upper support and lower support 130a and 130b, respectively, also include hinges 136a and 136b which, when the SULU 100 is assembled, matingly engage one another to allow pivotable movement between the supports 130a and 130b from an open position (FIG. 23) to a closed position (FIG. 2). Preferably, a pin 180 secures the two hinges 136a and 136b together (FIG. 6). Upper and lower supports 130a and 130b each include a longitudinally-extending opening 133a (FIG. 23) and 133b which aligns with openings 121a, 121b, 111a and 111b described above to receive saphenous vein 320 therethrough as seen best in FIGS. 17 and 18. Longitudinally oriented slots 131a and 131b are disposed adjacent openings 133a and 133b on the upper and lower support members 130a and 130b, respectively, for receiving locking tabs 116a and 116b in much the same manner as described above with respect to slots 126a and 126b of the second retracting sleeve 120.

Lower support 130b includes a pair of shoulders 132a and 132b disposed on opposite sides of opening 133b for slideably receiving a corresponding pair of flanges 144a and 144b associated with an upper locking sleeve 140a. More particularly, each flange 144a and 144b extends distally from the upper locking sleeve 140a to define a notch 149a and 149b, respectively, therein for receiving shoulders 132a and 132b of lower support 130b.

Upper locking sleeve 140a includes a C-shaped clip 146a (FIG. 8) disposed therein which has pair of opposing hooks 147a for snap-lockingly engaging slit 182a of locking tab 116a of first retracting sleeve 110. A lower locking sleeve 140b operates in a similar manner and includes a pair of opposing hooks 147b for snap-lockingly engaging slit 182b of locking tab 116b of first retracting sleeve 110. Upper locking sleeve 140a also includes an opening 141a which aligns with openings 133a, 133b, 121a, 121b, 111a and 111b described above to receive saphenous vein 320 therethrough as seen best in FIGS. 17 and 18. It is envisioned that upon retraction of the second retracting sleeve 120, upper locking sleeve 140a will move proximally relative to shoulders 132b and 134b and disengage shoulders 132a, 132b which, in turn, will allow the upper and lower supports 130a and 130b to pivot about pin 180 and release the saphenous vein 320 (FIGS. 21E and 23). This will be explained in greater detail with respect to the operation of the instrument as described below.

SULU 100 also includes a biasing post 102 which mechanically aligns upper and lower supports 130a and 130b in fixed relation relative to one another. More particularly, biasing post 102 includes a proximal end 103 and a distal end 105 and has a vertically oriented cavity 106 disposed therethrough for receiving tabs 138a and 138b of the upper and lower supports 130a and 130b, respectively. As mentioned above, tabs 138a and 138b pass through slots 114a, 114b of the first retracting sleeve 110 and through slots 101, 108 and 109 of the second retracting sleeve 120 and mechanically align with one another within cavity 106 as best seen in FIG. 21B.

Biasing post 102 also includes a tapered spacer 104 disposed along the outer periphery thereof for frictionally locking the first retracting sleeve 110 in a retracted position after the first retracting sleeve 110 is withdrawn by the first retractor 80. More particularly, when the SULU 100 is assembled and prior to firing the surgical instrument 10, biasing post 102 is disposed relative to the first retracting sleeve 110 such that spacer 104 is proximal to lip 112 (FIG. 13). During retraction of the first retracting sleeve 110, lip 112 is forced over spacer 104 and the first retracting sleeve 110 is locked into retracted position and prevented from recoiling. As explained in greater detail below, locking the first retracting sleeve 110 in a retracted position also pre-disposes the second retracting sleeve 120 for retraction relative to the first retracting sleeve (FIG. 22A).

Turning now in detail to the loading of the SULU 100 within actuator assembly 20 as best seen in FIG. 5, thumb tab 30 is moved proximally by way of thumb guide 35 against spring 38 which, in turn, moves sleeve 32 and protective cover 95 proximally to expose carriages 86 and 88. The SULU 100 is then loaded within actuator assembly 20 by placing lip 112 within carriage 88 and lip 122 within carriage 86. As best shown in FIG. 13, lip 122 is positioned near the distal end of carriage 86 which allows lip 122 and, hence, second retracting sleeve 120, to move independently from the first retracting sleeve upon activation of the second retractor 50. In contrast, carriage 88 is dimensioned smaller than carriage 86 such that lip 112 fits snugly within carriage 88. Once the SULU is positioned within carriages 86 and 88, thumb tab 30 is released and spring 38 biases sleeve 32 and protective cover 95 distally over lips 112 and 122 to lock the SULU 100 within the actuator assembly 20.

In use and as shown in FIGS. 17-24, surgical instrument 10 facilitates the performance of a vascular anastomosis and either eliminates and/or minimizes the need for manual suturing of the vessels. The method and usage described herein will be addressed in terms of vascular anastomosis performed on a beating heart. However, the presently disclosed surgical instrument 10 may also be used in performing anastomoses of other tubular or luminal body structures without departing from the scope of the present disclosure. For example, surgical instrument 10 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

Figure 25:
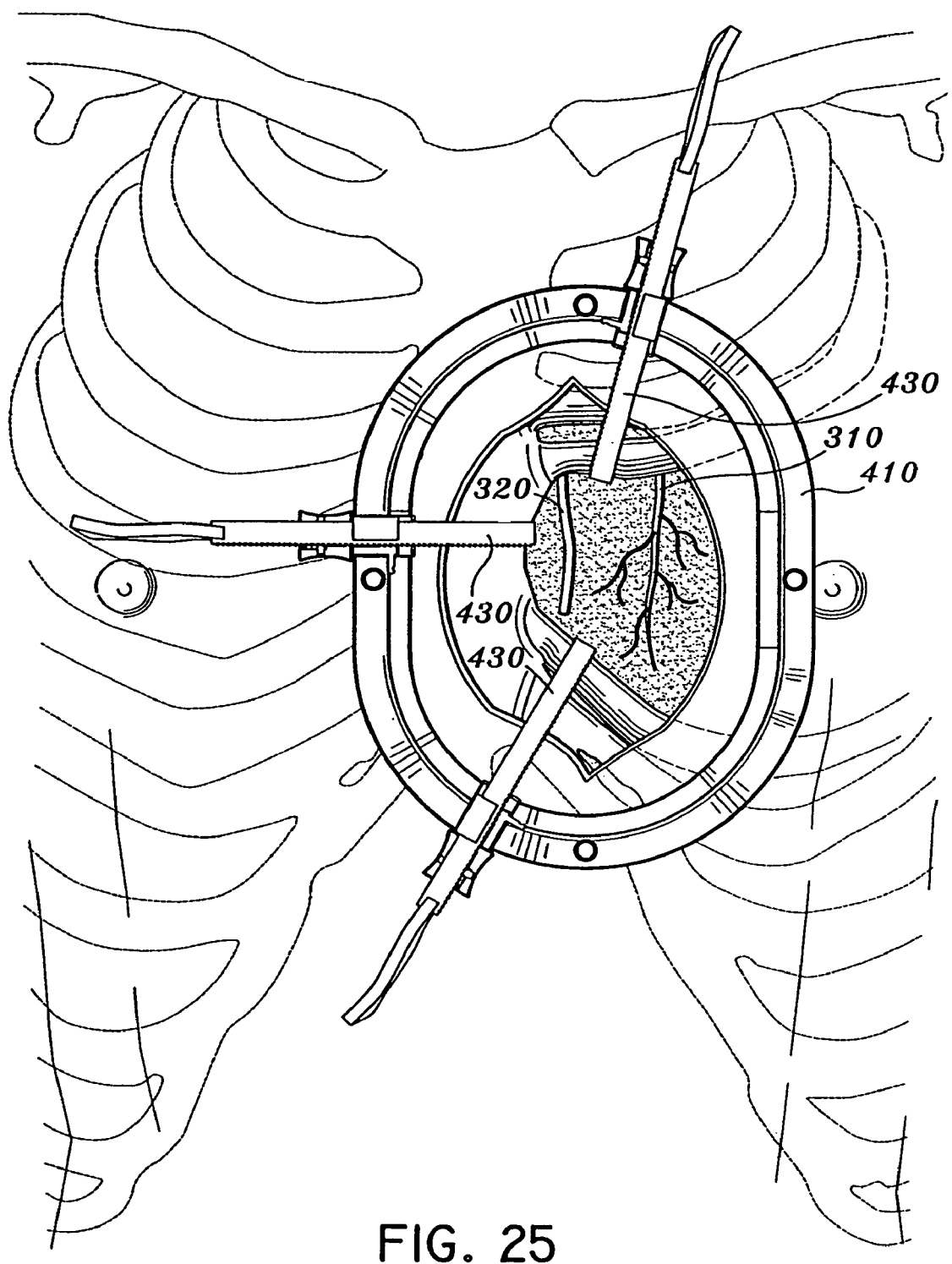
FIG. 25 is a view showing an operating "window" with the patient's heart exposed.

To gain access to the heart, after an incision is made, a surgical retractor assembly may be used to separate the ribs at the site of the incision as shown in FIG. 25. Specifically, a base 410 is placed on the chest of the patient with the central opening defined by the base being positioned over the operative site. Retractor assemblies 430 are mounted to the base 410 at various locations. Each retractor assembly 430 includes a blade having a hook to engage either a rib or the sternum therewith. The retractor assemblies are mounted and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure.

Once the desired access to the heart is achieved, the graft vessel, e.g., the saphenous vein 320 is dissected from the surrounding cartilage and muscle, and a free end of the vessel is exposed. The occluded coronary artery, e.g., the LAD and/or aorta 310, is then prepared for receiving the saphenous vein 320 graft. The heart is positioned in the desired orientation either by traction sutures passing through the pericardium or by manipulation with heart manipulation instruments which are held by the surgical personnel or clamped in a fixed orientation to a base such as the retractor assembly base. Blood flow through the LAD and/or aorta 310 can be restricted by cardiopulmonary bypass and pericardial cooling. Alternatively, a dampening instrument may be applied directly on the LAD and/or aorta 310 to restrict blood flow and reduce movement of the heart near the LAD and/or aorta 310.

Turning now in detail to the operation of the surgical instrument 10 and in particular, the operation of the SULU 100 as detailed in FIGS. 17-24, once the saphenous vein 320 has been harvested, the user inserts the free end 322 into opening 133 of the SULU and pull via a surgical hook or graspers the free end 322 towards the distal end of the SULU 100. The user then everts the saphenous vein 320 over the anvils 118a, 118b of the SULU 100 such that the free end 322 of the saphenous vein 320 is retained by end 269 of the surgical fasteners 260. Everting of the saphenous vein 320 may be achieved by any suitable known instruments and/or techniques such as by using graspers.

In some cases it may be preferable to orient the upper and lower supports 130a and 130b in a slightly longitudinally offset manner such that an angle is created relative to the transverse plane of the two supports 130a and 130b in order to optimize the anastomosis and to facilitate optimal blood flow across the graft site from the saphenous vein 320 to the LAD and/or aorta 310. This junction will create a more dramatically visible "heel" and "toe" effect in which an acute or obtuse angle between the vessels is clearly defined.

The remaining portion of the saphenous vein 320 is preferably positioned away from the instrument 10 to facilitate insertion of the saphenous vein 320 into the LAD and/or aorta 310 as shown in FIG. 18. The user then inserts the end of the SULU 100 into an incision 312 in the LAD and/or aorta such that the distal end 269 of each of the plurality of fasteners 260 and the everted end portions 322 of the saphenous vein 320 are sufficiently inserted into and through incision 312 (FIGS. 19 and 20). As seen best in the enlarged view of FIG. 20, the support leg 262, convexity 263 and prong 267 of each surgical fastener 260 remains outside incision 312. The instrument is now preset for firing.

FIGS. 21-22 show the firing sequence of instrument 10, i.e., when the handle 12 is depressed by the user. As best shown in FIGS. 21 and 21A, as handle 12 is depressed downwardly in the direction of reference arrow "A", lever 16 simultaneously imparts movement to both handle lock 40 and cam 60. More particularly, downward movement of handle 12 causes flanges 14a and 14b of lever 16 to urge flanges 42a and 42b of handle lock 40 distally against spring 45 in the direction of reference arrow "B" (FIG. 21). At the same time, handle 12 causes recess 17 of lever 16 to bias nub 66 which, in turn, causes cam 60 to deflect downwardly and proximally as best seen in FIG. 21A. Preferably, recess 17 in lever 16 is dimensioned to control the specific movement of nub 66 within recess 17 which, in turn, controls the overall movement of cam 60. Downward and proximal movement of cam 60 causes cam followers 51a and 51b to move within the first cam stages 64a and 62a of slots 64 and 62, respectively, which, in turn, moves the first retractor 80 and protective cover 95 proximally in the direction of reference arrow B.

As seen best in FIG. 21, as retractor 80 moves proximally as a result of the movement of cam followers 51a and 51b within slots 64 and 62, slot 85 moves proximally until it abuts pin 54. Preferably, when slot 85 abuts pin 54, cam 60 is forced more downwardly about pin 54 such that cam followers 51a and 51b move more proximally to engage the second stages 64b and 62b of the cam slots 64 and 62, respectively.

As mentioned above, the first retractor 80 retracts the first retracting sleeve 110 (FIG. 21) which, in turn, causes surgical fasteners 260 to deform as shown in FIGS. 21B and 21D. More particularly and as best shown in FIG. 21B, proximal movement of the first retractor 80 causes both the first retracting sleeve 110 and the second retracting sleeve 120 to move proximally relative to biasing post 102 until biasing post 102 abuts the end 69 of elongated stop 65. As a result, anvils 118a and 118b deform the distal ends 269 of surgical fasteners 260 upwardly and proximally towards braces 137a and 137b, respectively, i.e., arc-like distal ends 184a and 184b cause surgical fasteners 260 to deform upwardly and proximally upon retraction of the first retracting sleeve 110. At the same time, the LAD and/or aorta 310 is forced slightly proximally and extending prongs 267 penetrate to hold the LAD and/or aorta 310 in position as best seen in FIG. 22A.

It is anticipated that the radially offset orientation of the opposite ends 186a, 186b and 184a, 184b of the support channels 119a and 119b, respectively will cause the opposite ends 267 and 269 of the surgical fasteners 260 to deform at an angle ∀ relative to one another as best shown in FIG. 21D. This allows end 269 to deform proximal to braces 137a and 137b. Preferably, braces 137a and 137b have a tapered cross section to deform end 269 of surgical fastener 260 radially from end 267 during deformation.

FIG. 21C shows the resulting position of the spacer 104 of the biasing post 102 after the first retractor 80 retracts the first and second retracting sleeves 110 and 120, respectively. More particularly, spacer 104 frictionally locks the first retracting sleeve 110 relative to the second retracting sleeve 120 and prevents the first retracting sleeve 110 from recoiling after firing.

FIG. 21E shows the proximal movement of the locking sleeve 140a as a result of the movement of the first retracting sleeve 110. More particularly, when the first retracting sleeve 110 is retracted proximally, locking tab 116a retracts within slot 131a of support 130a and biases locking sleeve 140a in a proximal direction as well as seen by reference arrow "C".

Proximal movement of the locking sleeve 140*a* relative to support 130*a* disengages flanges 142*a* and 144*a* from shoulders 132*b* and 134*b*, respectively, of support 130*b* which, in turn, unlocks supports 130*a* and 130*b* from one another thus permitting pivotal movement of the support members 130*a*, 130*b* as best seen in FIGS. 21E and 23.

Continued downward movement of handle 12 results in both proximal movement of the second retractor 50 and engagement of the handle lock 40 with the handle 12. More particularly and as best illustrated in FIG. 22, as the user continues to move the handle 12 in a downward direction, flanges 14*a* and 14*b* clear corresponding flanges 42*a* and 42*b* and spring 45 biases handle lock 40 proximally in the direction of reference arrow "D" to lock the handle 12 in position. Simultaneously, cam 60 is rotated about pin 54 to a point where the second stages 64*a* and 62*a* of the cam slots 64 and 62 effect the movement of the cam followers 51*a* and 51*b*. More particularly, as cam 60 is forced downwardly, the second stage 62*a* of cam slot 62 moves cam follower 51*b* proximally which, in turn, moves the second retractor 50 proximally. The second stage 64*a* of cam slot 64 is generally vertically oriented and, as a result, cam follower 51*a* moves vertically upon continued downward movement of handle 12. Slot 57 of retractor 50 allows the second retractor 50 to slide proximally relative to cam follower 51*a*.

As mentioned above, second retractor 50 moves the key-like end 53 of the second retracting sleeve 120 within carriage 86 relative to the first retracting sleeve 110 as illustrated by reference arrow "E" of FIG. 22A. Proximal movement of the second retracting sleeve 120 retracts the prongs 127*a* and 127*b* of fingers 124*a*, 124*b*, respectively, which releases the surgical fasteners 260 as illustrated by reference arrow "E" of FIG. 22B.

As mentioned above, after sleeve 110 is retracted, locking sleeve 140*a* moves proximally to allow the two supports 130*a* and 130*b* to pivot away from one another as shown in FIG. 23 to permit the removal of the saphenous vein 320 from within the SULU thereby completing the vascular anastomosis as shown in FIG. 24.

Figure 26A:
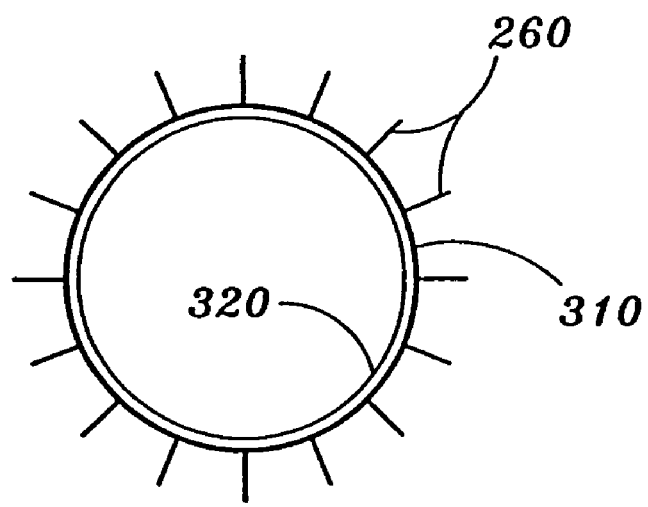
FIG. 26A is a view showing the surgical fastener staple pattern of the instrument described with respect to FIGS. 1-26.
Figure 26B:
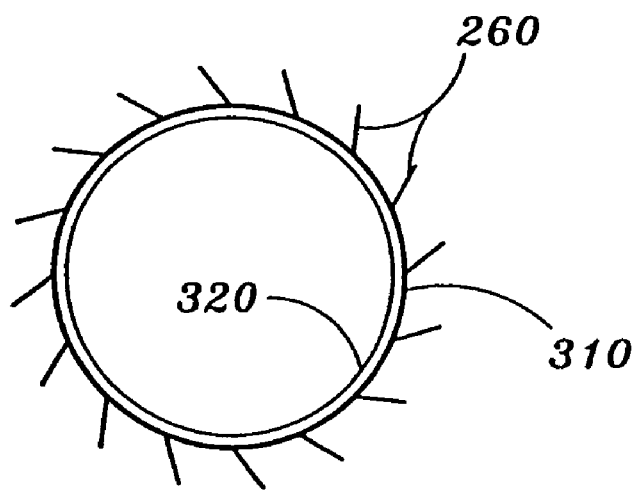
FIG. 26B. is a view showing one possible alternative surgical fastener staple pattern.

FIG. 26A shows a schematic diagram of the surgical fastener staple pattern which is formed upon actuation of the instrument described above with respect to FIGS. 1-26. More particularly, the surgical fasteners are supported by the fastener support braces 137*a*, 137*b* in a normal manner relative to a longitudinal axis "A" (FIG. 5) extending through the SULU. It is envisioned that other surgical fastener staple patterns, e.g., spiral, tangential or angular relative to axis "A", may be utilized to achieve hemostasis between vessels, FIG. 26B.

It will be understood that various modifications may be made to the embodiment shown herein. For example, the instrument may be sized to perform an anastomosis for other vessels and luminal tissue. Moreover, although the various internal components of the instrument 10 are shown engaged by particular mechanical interfaces it is envisioned that other types of mechanical interfaces can be employed to achieve the same or similar purpose, e.g., snap-fit, tongue and groove, press fit, etc. Therefore, the above description should not be construed as limiting, but merely as exemplifications of preferred embodiment. Those skilled in the art will envision other modifications within the scope and spirit of the claims appended hereto.

What is claimed is:

1. A surgical instrument for anastomosis of first and second blood vessels, comprising:
    a housing having distal and proximal ends;
    a loading unit having:
        a fastener support member for supporting a plurality of surgical fasteners;
        wherein an anvil supports the plurality of surgical fasteners in an initial position of the surgical instrument;
        first and second retracting sleeves movable relative to the fastener support member from a first position wherein the distal ends of the retracting sleeves are disposed relative to the fastener support member to a second position wherein the distal ends of the retracting sleeves are disposed in closer proximity to the fastener support member;
    an actuator which moves the first and second sleeves relative to the fastener support member; and
    a locking mechanism which locks the actuator to the housing after the instrument is fired.

2. The surgical instrument according to claim 1 wherein the actuator includes a handle.

3. The surgical instrument according to claim 1 wherein the loading unit includes two halves which are pivotable relative to one another.

4. The surgical instrument according to claim 3 wherein the two halves of the loading unit when closed form an elongated aperture which receives the second vessel therethrough.

5. The surgical instrument according to claim 1 wherein the distal end of the first sleeve includes a plurality of elongated channels which support the surgical fasteners.

6. The surgical instrument according to claim 5 wherein each elongated channel includes a distal and proximal end, each distal end of each elongated channel being radially offset from each corresponding proximal end of each elongated channel.

7. The surgical instrument according to claim 1 wherein the fastener support supports the surgical fasteners in an array-like manner.

8. The surgical instrument according to claim 5 wherein the second sleeve includes a plurality of resilient fingers which releasably secure the surgical fasteners within the elongated channels.

9. The surgical instrument according to claim 1 wherein continued movement of the actuator moves the second sleeve relative to the first sleeve.

10. The surgical instrument according to claim 1 wherein the actuator includes a cam.

11. The surgical instrument according to claim 1 wherein the actuator includes a multi-staged cam.

12. The surgical instrument according to claim 11 wherein a first stage of the multi-staged cam imparts movement to both the first and second sleeves and a second stage of the multi-staged cam imparts movement to the second sleeve relative to the first sleeve.

13. The surgical instrument according to claim 1 wherein the actuator includes at least one spring.

14. The surgical instrument according to claim 1 wherein the loading unit is releasably mounted to the housing.

15. The surgical instrument according to claim 1 wherein the instrument further comprises:
    a locking tab which selectively mounts the loading unit to the housing.

16. The surgical instrument according to claim 15 wherein the locking tab is movable from a first position which enables the loading unit to be mounted to the housing to a second position which secures the loading unit to the housing.

17. The surgical instrument according to claim 1 wherein the loading unit is disposable.

18. The surgical instrument according to claim 1 wherein the distal end of the first sleeve includes an anvil which retains the distal ends of the surgical fasteners and which supports an everted end of the second vessel.

19. The surgical instrument according to claim 18 wherein the anvil includes an angled surface which causes the distal end of the surgical fasteners to deform proximally during firing.

20. A surgical instrument for anastomosis of first and second blood vessels, comprising:
a housing having distal and proximal ends;
a loading unit having:
an anvil supporting a plurality of surgical fasteners in an initial position of the surgical instrument, the plurality of surgical fasteners being supported in an array like manner;
first and second retracting sleeves disposed between an upper and lower fastener support members, the retracting sleeves being movable relative to the fastener support members from a first position wherein the distal ends of the sleeves are disposed relative to the fastener support member to a second position wherein the distal ends of the sleeves are disposed in closer proximity to the fastener support members and wherein the first sleeve includes a base and a sleeve cap, the sleeve cap being selectively pivotable relative to the base; and
an actuator which moves the first and second sleeves relative to the fastener support member.

21. The surgical instrument according to claim 20 wherein the second sleeve is movable relative to the first sleeve.

22. The surgical instrument according to claim 21 wherein continued movement of the actuator moves the second sleeve relative to the first sleeve.

23. The surgical instrument according to claim 22 wherein the housing includes a second key-like arm which moves the second sleeve relative to the first sleeve.

24. The surgical instrument according to claim 20 wherein each of the fastener support members includes a plurality of radially inscribed channels which support the proximal end of the surgical fasteners.

25. The surgical instrument according to claim 20 wherein the distal end of the first retracting sleeve includes a plurality of elongated channels which support the surgical fasteners.

26. The surgical instrument according to claim 25 wherein each elongated channel includes a distal and proximal end wherein the distal end is radially offset from the proximal end.

27. The surgical instrument according to claim 25 wherein the second retracting sleeve includes a plurality of resilient fingers which releasably secure the surgical fasteners within the elongated channels of the first retracting sleeve.

28. The surgical instrument according to claim 20 wherein the loading unit further comprises:
a post which upon movement of the actuator biases the first and second retracting sleeves relative to the fastener support members.

29. The surgical instrument according to claim 28 wherein the post further comprises:
a spacer which locks the first retracting sleeve relative to the fastener support members to permit subsequent movement of the second retracting sleeve relative to the first retracting sleeve upon continued movement of the actuator.

30. The surgical instrument according to claim 20 wherein the loading unit is comprised of two halves which are pivotable relative to one another.

31. The surgical instrument according to claim 30 wherein the two halves of the loading unit when closed form an elongated aperture which receives the second vessel therethrough.

32. The surgical instrument according to claim 31 wherein prior to actuation of the handle, the two halves of the loading unit are pivotally secured relative to one another and upon actuation of the handle, the two halves are unsecured allowing the halves to pivot relative to one another to release the second vessel from within the aperture.

33. The surgical instrument according to claim 20 wherein the second retracting sleeve includes a plurality of resilient fingers which releasably secure the surgical fasteners within the elongated channels of the first retracting sleeve.

34. The surgical instrument according to claim 20 wherein the surgical fasteners are supported normally relative to a longitudinal axis extending through the loading unit.

35. The surgical instrument according to claim 20 wherein the surgical fasteners are supported in an angular manner relative to a longitudinal axis extending through the loading unit.

36. A surgical instrument for anastomosis of first and second blood vessels, comprising:
a housing having distal and proximal ends;
a loading unit having:
an anvil supporting a plurality of surgical fasteners in an initial position of the surgical instrument, the plurality of surgical fasteners being supported in an array like manner;
first and second retracting sleeves disposed between an upper and lower fastener support members, the retracting sleeves being movable relative to the fastener support members from a first position wherein the distal ends of the sleeves are disposed relative to the fastener support member to a second position wherein the distal ends of the sleeves are disposed in closer proximity to the fastener support members and wherein the second sleeve includes upper and lower cuffs, the upper cuff being disposed between the upper fastener support and the first retracting sleeve and the lower cuff being disposed between the lower fastener support and the first retracting sleeve; and
an actuator which moves the first and second sleeves relative to the fastener support member.

* * * * *